United States Patent
Johnston et al.

(10) Patent No.: US 8,471,075 B2
(45) Date of Patent: *Jun. 25, 2013

(54) PROCESSES FOR MAKING ETHANOL FROM ACETIC ACID

(75) Inventors: Victor J. Johnston, Houston, TX (US); Laiyuan Chen, Houston, TX (US); Barbara F. Kimmich, Bernardsville, NJ (US); Josefina T. Chapman, Houston, TX (US); James H. Zink, League City, TX (US); Heiko Weiner, Pasadena, TX (US); John L. Potts, Angleton, TX (US); Radmila Jevtic, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 680 days.

This patent is subject to a terminal disclaimer.

(21) Appl. No.: 12/698,947

(22) Filed: Feb. 2, 2010

(65) Prior Publication Data

US 2010/0197985 A1  Aug. 5, 2010

Related U.S. Application Data

(63) Continuation-in-part of application No. 12/588,727, filed on Oct. 26, 2009, now Pat. No. 8,309,772, which is a continuation-in-part of application No. 12/221,141, filed on Jul. 31, 2008, now Pat. No. 7,863,489.

(51) Int. Cl.
C07C 29/132 (2006.01)

(52) U.S. Cl.
USPC ........... 568/861; 568/700; 568/864; 568/883; 568/890

(58) Field of Classification Search
None
See application file for complete search history.

(56) References Cited

U.S. PATENT DOCUMENTS

| | | |
|---|---|---|
| 2,021,698 A | 11/1935 | Perkins |
| 2,105,540 A | 1/1938 | Lazier |
| 2,607,807 A | 8/1952 | Ford |
| 2,744,939 A | 5/1956 | Kennel |
| 2,882,244 A | 4/1959 | Milton |
| 3,130,007 A | 4/1964 | Breck |
| 3,478,112 A | 11/1969 | Adam |
| 3,702,886 A | 11/1972 | Argauer et al. |
| 3,729,429 A | 4/1973 | Robson |
| 3,990,952 A | 11/1976 | Katzen et al. |
| 4,065,512 A | 12/1977 | Cares |
| 4,228,307 A | 10/1980 | Zimmerschied |
| 4,270,015 A | 5/1981 | Knifton |
| 4,275,228 A | 6/1981 | Gruffaz et al. |
| 4,317,918 A | 3/1982 | Takano et al. |
| 4,328,373 A | 5/1982 | Strojny |
| 4,337,351 A | 6/1982 | Larkins, Jr. |
| 4,374,265 A | 2/1983 | Larkins, Jr. |
| 4,395,576 A | 7/1983 | Kwantes et al. |
| 4,398,039 A | 8/1983 | Pesa et al. |
| 4,399,305 A | 8/1983 | Schreck |
| 4,421,939 A | 12/1983 | Kiff et al. |
| 4,443,639 A | 4/1984 | Pesa et al. |
| 4,465,854 A | 8/1984 | Pond et al. |
| 4,471,136 A | 9/1984 | Larkins et al. |
| 4,480,115 A | 10/1984 | McGinnis |
| 4,517,391 A | 5/1985 | Schuster et al. |
| 4,521,630 A | 6/1985 | Wattimena et al. |
| 4,550,185 A | 10/1985 | Mabry et al. |
| 4,581,473 A | 4/1986 | Polichnowski |
| 4,613,700 A | 9/1986 | Maki et al. |
| 4,620,050 A | 10/1986 | Cognion et al. |
| 4,678,543 A | 7/1987 | Houben et al. |
| 4,692,218 A | 9/1987 | Houben et al. |
| 4,696,596 A | 9/1987 | Russell et al. |
| 4,777,303 A | 10/1988 | Kitson et al. |
| 4,804,791 A | 2/1989 | Kitson et al. |
| 4,826,795 A | 5/1989 | Kitson et al. |
| 4,843,170 A | 6/1989 | Isshiki et al. |
| 4,886,905 A | 12/1989 | Larkins, Jr. |
| 4,978,778 A | 12/1990 | Isshiki et al. |
| 4,985,572 A | 1/1991 | Kitson et al. |
| 4,990,655 A | 2/1991 | Kitson et al. |
| 5,008,235 A | 4/1991 | Wegman |
| 5,061,671 A | 10/1991 | Kitson et al. |
| 5,124,004 A | 6/1992 | Grethlein et al. |
| 5,137,861 A | 8/1992 | Shih et al. |

(Continued)

FOREIGN PATENT DOCUMENTS

CN 1230458 10/1999
EP 0137749 A2 4/1984

(Continued)

OTHER PUBLICATIONS

English language abstract for JP 11147845 A, Jun. 2, 1999.
English language translation of JP H06-116182, Apr. 26, 1994.
Spivey et al., "Heterogeneous catalytic synthesis of ethanol from biomass-dervied syngas," Chemical Society Review, 2007, vol. 36, pp. 1514-1528.
Subramani et al., "A Review of Recent Literature to Search for an Efficient Catalytic Process for the Conversion of Syngas to Ethanol," Energy & Fuels, 2008, vol. 22, pp. 814-839.
Notice of Allowance in U.S. Appl. No. 12/588,727, mailed Aug. 27, 2012.
Djerboua, et al., "On the performance of a highly loadedCO/SiO2 catalyst in the gas phase hydrogenation of crotonaldehyde thermal treatments—catalyst structure-selectivity relationship," Applied Catalysis A: General (2005), 282, p. 123-133.

(Continued)

Primary Examiner — Johann R Richter
Assistant Examiner — Pancham Bakshi

(57) ABSTRACT

A process for selective formation of ethanol from acetic acid by hydrogenating acetic acid in the presence of first metal, a silicaceous support, and at least one support modifier. Preferably, the first metal is selected from the group consisting of copper, iron, cobalt, nickel, ruthenium, rhodium, palladium, osmium, iridium, platinum, titanium, zinc, chromium, rhenium, molybdenum, and tungsten. In addition the catalyst may comprise a second metal preferably selected from the group consisting of copper, molybdenum, tin, chromium, iron, cobalt, vanadium, tungsten, palladium, platinum, lanthanum, cerium, manganese, ruthenium, rhenium, gold, and nickel.

7 Claims, 6 Drawing Sheets

U.S. PATENT DOCUMENTS

| | | | |
|---|---|---|---|
| 5,149,680 A * | 9/1992 | Kitson et al. | 502/185 |
| 5,155,084 A | 10/1992 | Horn et al. | |
| 5,185,308 A | 2/1993 | Bartley et al. | |
| 5,241,106 A | 8/1993 | Inoue et al. | |
| 5,243,095 A | 9/1993 | Roberts et al. | |
| 5,306,845 A | 4/1994 | Yokohama et al. | |
| 5,350,504 A | 9/1994 | Dessau et al. | |
| 5,426,246 A | 6/1995 | Nagahara et al. | |
| 5,475,144 A | 12/1995 | Watson et al. | |
| 5,476,827 A | 12/1995 | Ferrero et al. | |
| RE35,377 E | 11/1996 | Steinberg et al. | |
| 5,585,523 A | 12/1996 | Weiguny et al. | |
| 5,691,267 A | 11/1997 | Nicolau et al. | |
| 5,719,315 A | 2/1998 | Tustin et al. | |
| 5,731,456 A | 3/1998 | Tustin et al. | |
| 5,767,307 A | 6/1998 | Ramprasad et al. | |
| 5,821,111 A | 10/1998 | Grady | |
| 5,849,657 A | 12/1998 | Rotgerink | |
| 5,861,530 A | 1/1999 | Atkins et al. | |
| 5,945,570 A | 8/1999 | Arhancet et al. | |
| 5,955,397 A | 9/1999 | Didillon | |
| 5,973,193 A | 10/1999 | Crane et al. | |
| 6,008,384 A * | 12/1999 | Bockrath et al. | 549/508 |
| 6,040,474 A | 3/2000 | Jobson et al. | |
| 6,049,008 A | 4/2000 | Roberts et al. | |
| 6,093,845 A | 7/2000 | Van Acker et al. | |
| 6,114,571 A | 9/2000 | Abel et al. | |
| 6,121,498 A | 9/2000 | Tustin et al. | |
| 6,232,352 B1 | 5/2001 | Vidalin et al. | |
| 6,232,504 B1 | 5/2001 | Barteau et al. | |
| 6,294,703 B1 | 9/2001 | Hara et al. | |
| 6,462,231 B1 | 10/2002 | Yanagawa et al. | |
| 6,472,555 B2 | 10/2002 | Choudary et al. | |
| 6,486,366 B1 | 11/2002 | Ostgard et al. | |
| 6,495,730 B1 | 12/2002 | Konishi et al. | |
| 6,509,180 B1 | 1/2003 | Verser et al. | |
| 6,509,290 B1 | 1/2003 | Vaughn et al. | |
| 6,559,333 B1 | 5/2003 | Brunelle | |
| 6,603,038 B1 | 8/2003 | Hagemeyer et al. | |
| 6,632,330 B1 | 10/2003 | Colley | |
| 6,657,078 B2 | 12/2003 | Scates et al. | |
| 6,685,754 B2 | 2/2004 | Kindig et al. | |
| 6,693,213 B1 | 2/2004 | Kolena et al. | |
| 6,696,596 B1 | 2/2004 | Herzog et al. | |
| 6,727,380 B2 | 4/2004 | Ellis et al. | |
| 6,765,110 B2 | 7/2004 | Warner et al. | |
| 6,768,021 B2 | 7/2004 | Horan et al. | |
| 6,812,372 B2 | 11/2004 | Janssen et al. | |
| 6,852,877 B1 | 2/2005 | Zeyss et al. | |
| 6,903,045 B2 | 6/2005 | Zoeller | |
| 6,906,228 B2 | 6/2005 | Fischer et al. | |
| 6,927,048 B2 | 8/2005 | Verser et al. | |
| 7,074,603 B2 | 7/2006 | Verser et al. | |
| 7,084,312 B2 | 8/2006 | Huber et al. | |
| 7,297,236 B1 | 11/2007 | Vander et al. | |
| 7,351,559 B2 | 4/2008 | Verser et al. | |
| 7,375,049 B2 | 5/2008 | Hayes | |
| 7,425,657 B1 | 9/2008 | Elliott et al. | |
| 7,507,562 B2 | 3/2009 | Verser et al. | |
| 7,518,014 B2 | 4/2009 | Kimmich | |
| 7,538,060 B2 | 5/2009 | Bernicki et al. | |
| 7,553,397 B1 | 6/2009 | Colley et al. | |
| 7,572,353 B1 | 8/2009 | Vander et al. | |
| 7,608,744 B1 | 10/2009 | Johnston et al. | |
| 7,863,489 B2 | 1/2011 | Johnston | |
| 7,884,253 B2 | 2/2011 | Stites | |
| 2003/0013908 A1 | 1/2003 | Horan et al. | |
| 2003/0077771 A1 | 4/2003 | Verser et al. | |
| 2003/0104587 A1 | 6/2003 | Verser et al. | |
| 2003/0114719 A1 | 6/2003 | Fischer et al. | |
| 2003/0191020 A1 | 10/2003 | Bharadwaj | |
| 2004/0195084 A1 | 10/2004 | Hetherington et al. | |
| 2006/0019360 A1 | 1/2006 | Verser et al. | |
| 2006/0102520 A1 | 5/2006 | Lapinski | |
| 2006/0106246 A1 | 5/2006 | Warner et al. | |
| 2006/0127999 A1 | 6/2006 | Verser et al. | |
| 2007/0270511 A1 | 11/2007 | Melnichuk | |
| 2008/0207953 A1 | 8/2008 | Houssin et al. | |
| 2009/0005588 A1 | 1/2009 | Hassan et al. | |
| 2009/0023192 A1 | 1/2009 | Verser et al. | |
| 2009/0081749 A1 | 3/2009 | Verser et al. | |
| 2009/0166172 A1 | 7/2009 | Casey et al. | |
| 2009/0221725 A1 | 9/2009 | Chornet et al. | |
| 2009/0318573 A1 | 12/2009 | Stites et al. | |
| 2009/0326080 A1 | 12/2009 | Chornet et al. | |
| 2010/0016454 A1 | 1/2010 | Gracey et al. | |
| 2010/0029980 A1 | 2/2010 | Johnston et al. | |
| 2010/0029995 A1 | 2/2010 | Johnston et al. | |
| 2010/0029996 A1 | 2/2010 | Danjo et al. | |
| 2010/0113843 A1 | 5/2010 | Lee | |
| 2010/0121114 A1 | 5/2010 | Weiner et al. | |
| 2010/0168493 A1 | 7/2010 | Le Peltier | |
| 2010/0196789 A1 | 8/2010 | Fisher | |
| 2010/0249479 A1 | 9/2010 | Berg-Slot | |
| 2011/0282109 A1 * | 11/2011 | Johnston et al. | 568/885 |
| 2012/0253085 A1 * | 10/2012 | Johnston et al. | 568/885 |

FOREIGN PATENT DOCUMENTS

| | | |
|---|---|---|
| EP | 0167300 A1 | 1/1986 |
| EP | 0175558 | 3/1986 |
| EP | 0192587 | 8/1986 |
| EP | 0198682 B1 | 10/1986 |
| EP | 0285786 B1 | 5/1988 |
| EP | 0372847 A2 | 6/1990 |
| EP | 0400904 | 12/1990 |
| EP | 0408528 | 1/1991 |
| EP | 0285420 B1 | 10/1991 |
| EP | 0990638 | 4/2000 |
| EP | 1262234 | 12/2002 |
| EP | 1277826 | 1/2003 |
| EP | 2060553 A1 | 5/2009 |
| EP | 2060555 A1 | 5/2009 |
| EP | 2186787 | 5/2010 |
| GB | 1168785 | 10/1969 |
| GB | 1559540 | 1/1980 |
| GB | 2136704 | 9/1987 |
| JP | 6116182 | 4/1994 |
| JP | 10-306047 A | 11/1998 |
| JP | 11147845 | 6/1999 |
| JP | 2001-046874 A | 2/2001 |
| JP | 2001-157841 A | 6/2001 |
| WO | WO 83/03409 A1 | 10/1983 |
| WO | WO 03/040037 A1 | 5/2003 |
| WO | 2005102513 | 1/2005 |
| WO | WO 2009/009322 A1 | 1/2009 |
| WO | WO 2009/009323 A1 | 1/2009 |
| WO | WO 2009/063176 A1 | 5/2009 |
| WO | 2009086839 | 7/2009 |
| WO | WO 2009/105860 A1 | 9/2009 |
| WO | WO 2010/014145 | 2/2010 |
| WO | WO 2010/014151 A2 | 2/2010 |
| WO | WO 2010/014153 A2 | 2/2010 |
| WO | WO 2010/055285 A1 | 5/2010 |
| WO | WO 2011/053365 | 5/2011 |

OTHER PUBLICATIONS

Ammari, et al. "An emergent catalytic material: Pt/ZnO catalyst for selective hydrogenation of crotonaldehyde," J. Catal. (2004) 221, p. 32-42.

Ammari, et al. "Selective hydrogenation of crotonaldehyde on Pt/ZnCl2/SiO2 catalysts," J. Catal. (2005), 235, p. 1-9.

Consonni, et al. "High Performances of Pt/ZnO Catalysts in Selective Hydrogenation of Crotonaldehyde," J. Catal. (1999), 188, p. 165-175.

Nitta, et al. "Selective hydrogenation of αβ-unsaturated aldehydes on cobalt—silica catalysts obtained from cobalt chrysotile", Applied Catal. (1989), 56, p. 9-22.

T. Yokoyama et al., "Fine chemicals through heterogeneous catalysis. Carboxylic acids and derivitatives." 2001, pp. 370-379.

English language abstract for CN1230458, Oct. 6, 1999.

Rachmady, Acetic Acid Reduction by $H_2$ on Bimetallic Pt—Fe Catalysts, Journal of Catalysis 209, 87-98 (Apr. 1, 2002), Elsevier Science (USA).

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Ordóñez et al., The role of metal and support sites on the hydrogenation of acetic acid on Ru-based catalysts, $21^{ST}$ NAM San Francisco, CA, Jun. 10, 2009.

Pestman et al., The formation of ketones and aldehydes from carboxylic acids, structure-activity relationship for two competitive reactions, Journal of Molecular Catalysis A: Chemical 103 Jun. 14, 1995, 175-180.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

ZeaChem, Inc., Technology Overview, Lakewood, Colorado www.zeachem.com, 2008.

Brunauer Emmett and Teller, J. Am. Chem. Soc. 60, 309 (1938).

Proc. Roy Soc. A314, pp. 473-498 (1970).

International Search Report and Written Opinion for PCT/US2009/004197 mailed Mar. 24, 2010 (14 pages).

International Search Report and Written Opinion for PCT/US2009/004195 mailed Mar. 26, 2010 (12 pages).

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Zheng, et al., (2007). Preparation and catalytic properties of a bimetallic Sn-Pt complex in the supercages of NaY zeolite by use of surface organometallic chemistry, Applied Organometallic Chemistry, 21(10), 836-840.

Santori et al., (2000). Hydrogenation of carbonylic compounds on Pt/SiO2 catalysts modified with SnBu4, Studies in Surface Science and Catalysis, 130, 2063-2068.

Acala, et al., (2005). Experimental and DFT studies of the conversion of ethanol and acetic acid on PtSn-based catalysts, Journal of Physical Chemistry, 109(6), 2074-2085.

International Search Report and Written Opinion for PCT/US2010/022947 mailed Jun. 7, 2010.

U.S. Office Action mailed Oct. 15, 2012 in co-pending U.S. Appl. No. 12/850,414.

U.S. Office Acton mailed Oct. 24, 2012 in co-pending U.S. Appl. No. 13/179,955.

U.S. Office Action mailed Nov. 29, 2012 in co-pending U.S. Appl. No. 12/699,024.

* cited by examiner

FIG. 1A - Selectivity Pt/Sn Catalyst
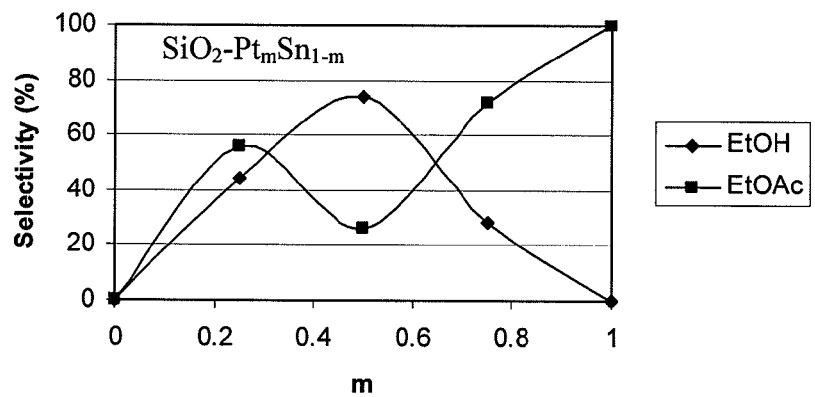
FIG. 1B - Productivity of Pt/Sn Catalyst
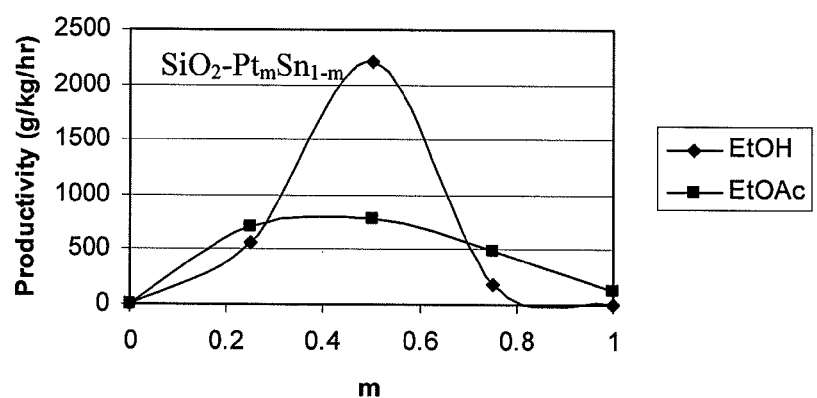
FIG. 1C - Conversion of HOAc
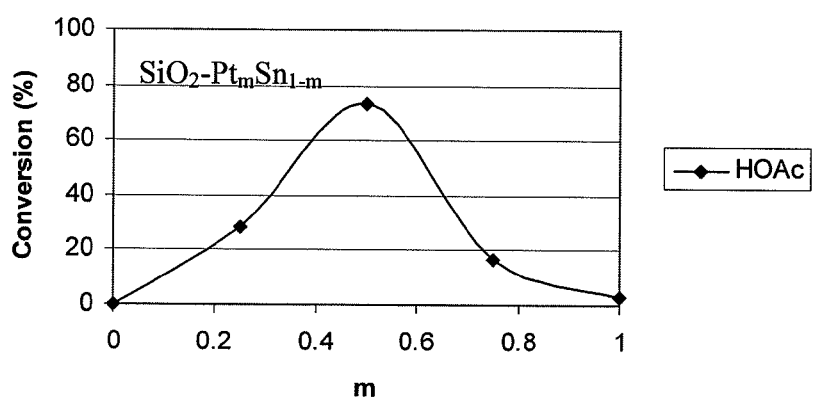

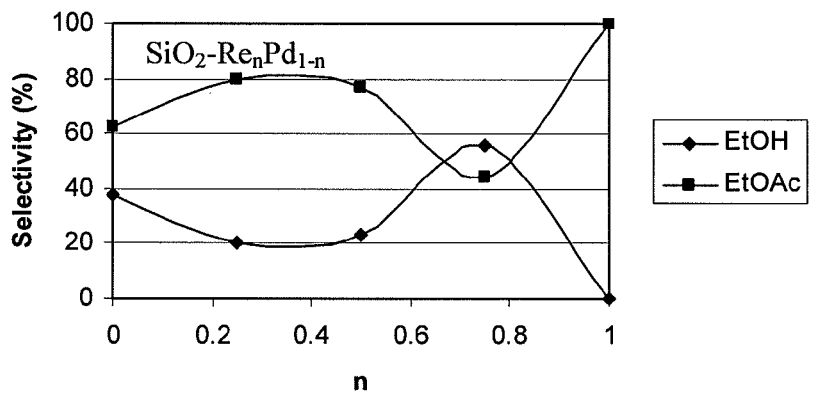
FIG. 2A - Selectivity of Re/Pd
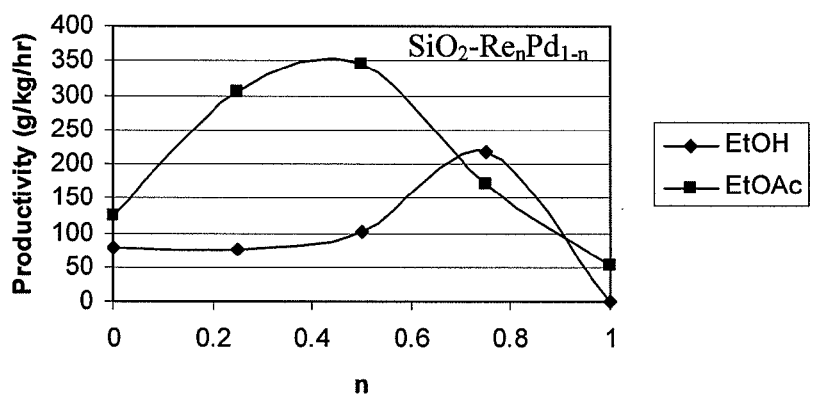
FIG. 2B - Productivity of Re/Pd
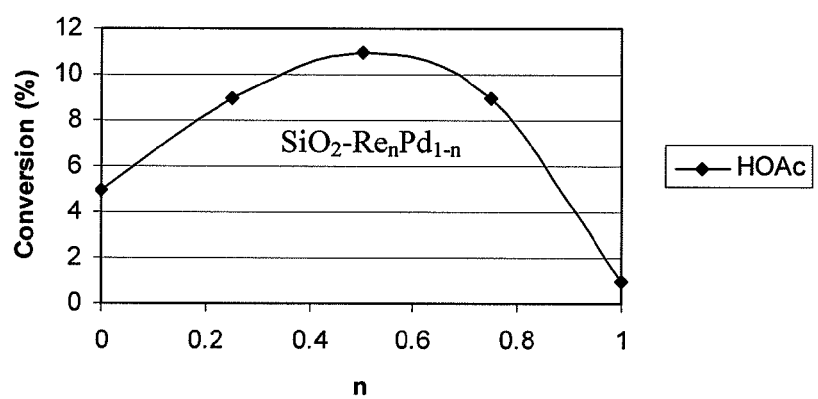
FIG. 2C - Conversion of HOAc

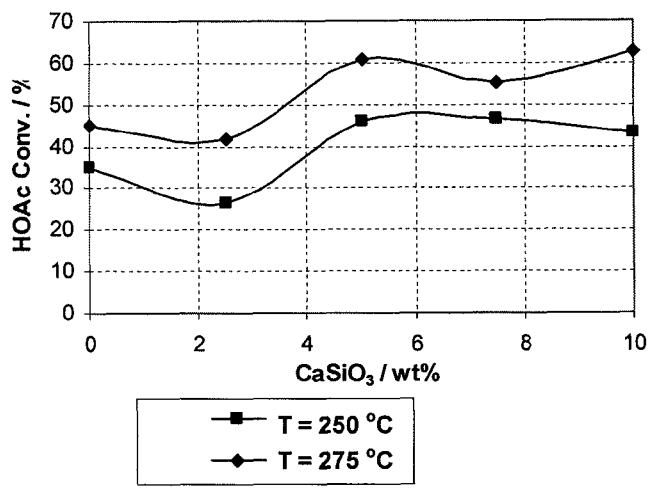
FIG. 6A - Conversion
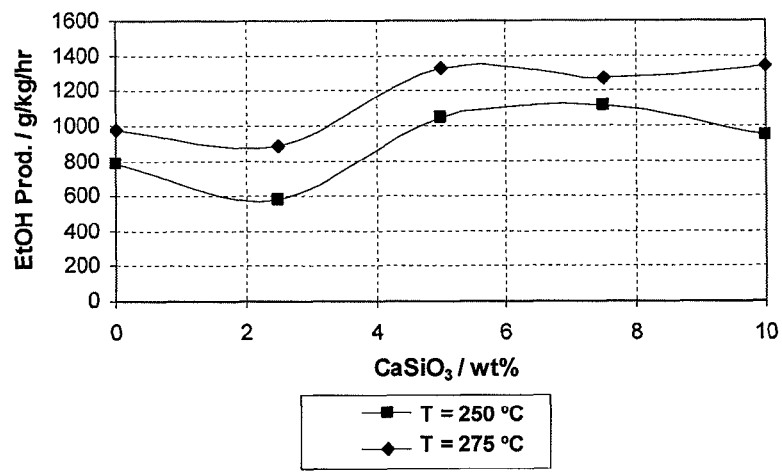
FIG. 6B - Productivity

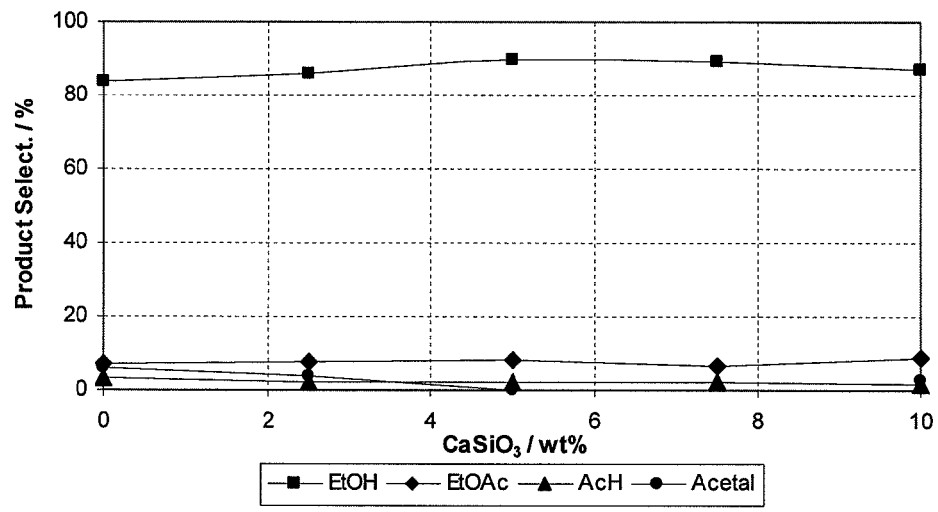
FIG. 6C - Selectivity @ 250
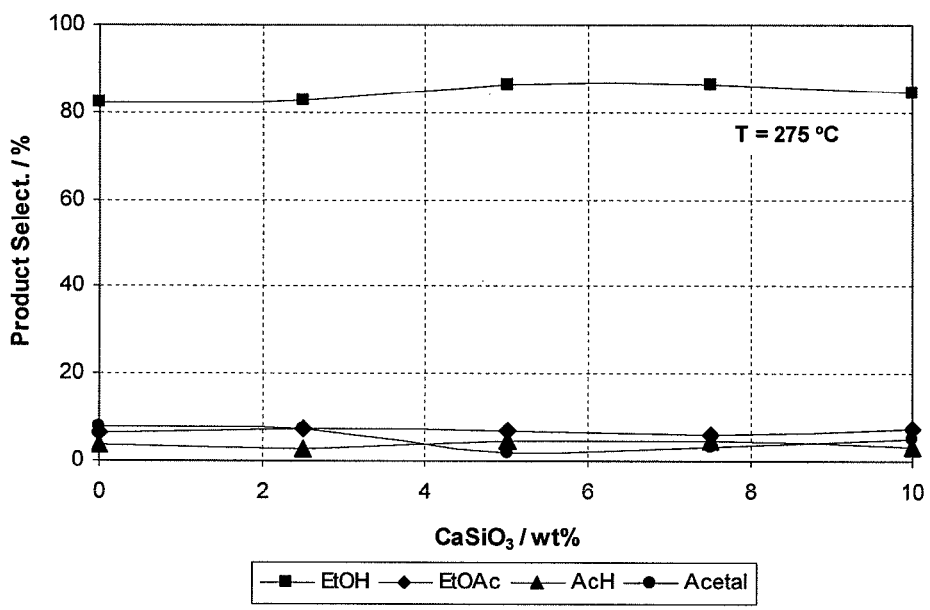
FIG. 6D - Selectivity @ 275

PROCESSES FOR MAKING ETHANOL FROM ACETIC ACID

CROSS REFERENCE TO RELATED APPLICATIONS

This is a continuation-in-part of U.S. application Ser. No. 12/588,727, filed Oct. 26, 2009, entitled "Tunable Catalyst Gas Phase Hydrogenation of Carboxylic Acids," and of U.S. application Ser. No. 12/221,141, filed Jul. 31, 2008, entitled "Direct and Selective Production of Ethanol from Acetic Acid Utilizing a Platinum/Tin Catalyst," the entireties of which are incorporated herein by reference.

FIELD OF THE INVENTION

The present invention relates generally to processes for hydrogenating acetic acid to form ethanol and to novel catalysts for use in such processes, the catalysts having high selectivities for ethanol.

BACKGROUND OF THE INVENTION

There is a long felt need for an economically viable process to convert acetic acid to ethanol which may be used in its own right or subsequently converted to ethylene which is an important commodity feedstock as it can be converted to vinyl acetate and/or ethyl acetate or any of a wide variety of other chemical products. For example, ethylene can also be converted to numerous polymer and monomer products. Fluctuating natural gas and crude oil prices contribute to fluctuations in the cost of conventionally produced, petroleum or natural gas-sourced ethylene, making the need for alternative sources of ethylene all the greater when oil prices rise.

Catalytic processes for reducing alkanoic acids and other carbonyl group containing compounds have been widely studied, and a variety of combinations of catalysts, supports and operating conditions have been mentioned in the literature. The reduction of various carboxylic acids over metal oxides is reviewed by T. Yokoyama et al. in "Fine chemicals through heterogeneous catalysis. Carboxylic acids and derivatives." Chapter 8.3.1, summarizes some of the developmental efforts for hydrogenation catalysts for various carboxylic acids. (Yokoyama, T.; Setoyama, T. "Carboxylic acids and derivatives." in: "Fine chemicals through heterogeneous catalysis." 2001, 370-379.)

A series of studies by M. A. Vannice et al. concern the conversion of acetic acid over a variety of heterogeneous catalysts (Rachmady W.; Vannice, M. A.; *J. Catal.* (2002) Vol. 207, pg. 317-330.) The vapor-phase reduction of acetic acid by $H_2$ over both supported and unsupported iron was reported in a separate study. (Rachmady, W.; Vannice, M. A. *J. Catal.* (2002) Vol. 208, pg. 158-169.) Further information on catalyst surface species and organic intermediates is set forth in Rachmady, W.; Vannice, M. A., *J. Catal.* (2002) Vol. 208, pg. 170-179). Vapor-phase acetic acid hydrogenation was studied further over a family of supported Pt—Fe catalysts in Rachmady, W.; Vannice, M. A. *J. Catal.* (2002) Vol. 209, pg. 87-98) and Rachmady, W.; Vannice, M. A. *J. Catal.* (2000) Vol. 192, pg. 322-334).

Various related publications concerning the selective hydrogenation of unsaturated aldehydes may be found in (Djerboua, F.; Benachour, D.; Touroude, R. Applied Catalysis A: General 2005, 282, 123-133; Liberkova, K.; Tourounde, R. *J. Mol. Catal.* 2002, 180, 221-230; Rodrigues, E. L.; Bueno, J. M. C. Applied Catalysis A: General 2004, 257, 210-211; Ammari, F.; Lamotte, J.; Touroude, R. *J. Catal.* 2004, 221, 32-42; Ammari, F.; Milone, C.; Touroude, R. *J. Catal.* 2005, 235, 1-9; Consonni, M.; Jokic, D.; Murzin, D. Y.; Touroude, R. *J. Catal.* 1999, 188, 165-175; Nitta, Y.; Ueno, K.; Imanaka, T.; Applied Catal. 1989, 56, 9-22.)

Studies reporting activity and selectivity over cobalt, platinum and tin-containing catalysts in the selective hydrogenation of crotonaldehyde to the unsaturated alcohol are found in R. Touroude et al. (Djerboua, F.; Benachour, D.; Touroude, R. Applied Catalysis A: General 2005, 282, 123-133 as well as Liberkova, K.; Tourounde, R.; *J. Mol. Catal.* 2002, 180, 221-230) as well as K. Lazar et al. (Lazar, K.; Rhodes, W. D.; Borbath, I.; Hegedues, M.; Margitfalvi, I. L. *Hyperfine Interactions* 2002, 1391140, 87-96.)

M. Santiago et al. (Santiago, M. A. N.; Sanchez-Castillo, M. A.; Cortright, R. D.; Dumesic, I. A. *J. Catal.* 2000, 193, 16-28.) discuss microcalorimetric, infrared spectroscopic, and reaction kinetics measurements combined with quantum-chemical calculations.

Catalytic activity in for the acetic acid hydrogenation has also been reported for heterogeneous systems with rhenium and ruthenium. (Ryashentseva, M. A.; Minachev, K. M.; Buiychev, B. M.; Ishchenko, V. M. Bull. *Acad Sci. USSR* 1988, 2436-2439).

U.S. Pat. No. 5,149,680 to Kitson et al. describes a process for the catalytic hydrogenation of carboxylic acids and their anhydrides to alcohols and/or esters utilizing platinum group metal alloy catalysts. U.S. Pat. No. 4,777,303 to Kitson et al. describes a process for the productions of alcohols by the hydrogenation of carboxylic acids. U.S. Pat. No. 4,804,791 to Kitson et al. describes another process for the production of alcohols by the hydrogenation of carboxylic acids. See also U.S. Pat. Nos. 5,061,671; 4,990,655; 4,985,572; and 4,826, 795.

Malinowski et al. (*Bull. Soc. Chim. Belg.* (1985), 94(2), 93-5), discuss reaction catalysis of acetic acid on low-valent titanium heterogenized on support materials such as silica ($SiO_2$) or titania ($TiO_2$).

Bimetallic ruthenium-tin/silica catalysts have been prepared by reaction of tetrabutyl tin with ruthenium dioxide supported on silica. (Loessard et al., *Studies in Surface Science and Catalysis* (1989), Volume Date 1988, 48 (*Struct. React. Surf.*), 591-600.)

The catalytic reduction of acetic acid has also been studied in, for instance, Hindermann et al., (Hindermann et al., *J. Chem. Res., Synopses* (1980), (11), 373), disclosing catalytic reduction of acetic acid on iron and on alkali-promoted iron.

Existing processes suffer from a variety of issues impeding commercial viability including: (i) catalysts without requisite selectivity to ethanol; (ii) catalysts which are possibly prohibitively expensive and/or nonselective for the formation of ethanol and that produce undesirable by-products; (iii) operating temperatures and pressures which are excessive; and/or (iv) insufficient catalyst life.

SUMMARY OF THE INVENTION

The present invention relates to processes for hydrogenating acetic acid to make ethanol at high selectivities. In a first embodiment, the invention is directed to a process for producing ethanol, comprising hydrogenating acetic acid in the presence of a catalyst comprising a first metal, a silicaceous support, and at least one support modifier. The first metal may be selected from the group consisting of Group IB, IIB, IIIB, IVB, VB, VIB, VIIB, or VIII transitional metal, a lanthanide metal, an actinide metal or a metal from any of Groups IIIA, IVA, VA, or VIA. More preferably the first metal may be selected from the group consisting of copper, iron, cobalt, nickel, ruthenium, rhodium, palladium, osmium, iridium, platinum, titanium, zinc, chromium, rhenium, molybdenum, and tungsten. The first metal may be present in an amount of from 0.1 to 25 wt. %, based on the total weight of the catalyst.

In another aspect, the catalyst may comprise a second metal (preferably different from the first metal), which may be selected from the group consisting of copper, molybdenum, tin, chromium, iron, cobalt, vanadium, tungsten, palladium, platinum, lanthanum, cerium, manganese, ruthenium, rhenium, gold, and nickel. In this aspect, the first metal may be present, for example, in an amount of from 0.1 to 10 wt. % and the second metal may be present in an amount of from 0.1 to 10 wt. %, based on the total weight of the catalyst. In another aspect, the catalyst may comprise a third metal (preferably different from the first metal and the second metal), which may be selected from the group consisting of cobalt, palladium, ruthenium, copper, zinc, platinum, tin, and rhenium and/or which may be present in an amount of 0.05 and 4 wt. %, based on the total weight of the catalyst.

Preferably, the first metal is platinum and the second metal is tin having a molar ratio of platinum to tin being from 0.4:0.6 to 0.6:0.4. In another preferred combination, the first metal is palladium and the second metal is rhenium having molar ratio of rhenium to palladium being from 0.7:0.3 to 0.85:0.15.

In a preferred aspect of the process, at least 10% of the acetic acid is converted during hydrogenation. Optionally, the catalysts have a selectivity to ethanol of at least 80% and/or a selectivity to methane, ethane, and carbon dioxide of less than 4%. In one embodiment, the catalyst has a productivity that decreases less than 6% per 100 hours of catalyst usage.

The silicaceous support may optionally be selected from the group consisting of silica, silica/alumina, calcium metasilicate, pyrogenic silica, high purity silica, and mixtures thereof and may be present in an amount of 25 wt. % to 99 wt. %, based on the total weight of the catalyst. Preferably, the silicaceous support has a surface area of from 50 m²/g to 600 m²/g.

The support modifier, e.g., metasilicate support modifier, may be selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. As one option, the support modifier may be selected from the group consisting of oxides and metasilicates of sodium, potassium, magnesium, calcium, scandium, yttrium, and zinc, preferably being CaSiO₃. The support modifier may be present in an amount of 0.1 wt. % to 50 wt. %, based on the total weight of the catalyst.

In one embodiment, the hydrogenation is performed in a vapor phase at a temperature of from 125° C. to 350° C., a pressure of 10 KPa to 3000 KPa, and a hydrogen to acetic acid mole ratio of greater than 4:1.

In another embodiment, the invention relates to a crude ethanol product (optionally obtained from the hydrogenation of acetic acid, as discussed above), which comprises (a) ethanol in an amount from 15 to 70 wt. %, preferably from 20 to 50 wt. % or, more preferably, from 25 to 50 wt. %; (b) acetic acid in an amount from 0 to 80 wt. %, preferably from 20 to 70 wt. % or, more preferably from 44 to 65 wt. %; (c) water in an amount from 5 to 30 wt. %, preferably from 10 to 30 wt. % or, more preferably, from 10 to 26 wt; and (d) any other compounds in an amount less than 10 wt. %, wherein all weight percents are based on the total weight of the crude ethanol product. A preferred crude ethanol product comprises the ethanol in an amount from 20 to 50 wt. %; the acetic acid in an amount from 28 to 70 wt. %; the water in an amount from 10 to 30 wt. %; and any other compounds in an amount less than 6 wt. %. An additional preferred crude ethanol product comprises the ethanol in an amount from 25 to 50 wt. %; the acetic acid in an amount from 44 to 65 wt. %; the water in an amount from 10 to 26 wt. %; and any other compounds in an amount less than 4 wt. %.

In another embodiment, the invention relates to a process for producing ethanol comprising hydrogenating acetic acid in the presence of a catalyst comprising:

$$Pt_v Pd_w Re_x Sn_y Ca_p Si_q O_r,$$

wherein: (i) the ratio of v:y is between 3:2 and 2:3, and/or (ii) the ratio of w:x is between 1:3 and 1:5; and p and q are selected such that p:q is from 1:20 to 1:200 with r being selected to satisfy valence requirements and v and w being selected such that:

$$0.005 \leq \frac{(3.25v + 1.75w)}{q} \leq 0.05.$$

In yet another embodiment, the invention relates to a process for producing ethanol comprising hydrogenating acetic acid in the presence of a catalyst comprising:

$$Pt_v Pd_w Re_x Sn_y Al_z Ca_p Si_q O_r,$$

wherein: (i) v and y are between 3:2 and 2:3, and/or (ii) w and x are between 1:3 and 1:5; and p and z and the relative locations of aluminum and calcium atoms present are controlled such that Brønsted acid sites present upon the surface thereof are balanced by a support modifier; and p and q are selected such that p:q is from 1:20 to 1:200 with r being selected to satisfy valence requirements, and v and w are selected such that:

$$0.005 \leq \frac{(3.25v + 1.75w)}{q} \leq 0.05.$$

BRIEF DESCRIPTION OF DRAWINGS

The invention is described in detail below with reference to the appended drawings, wherein like numerals designate similar parts.

FIG. 1A is a graph of the selectivity to ethanol and ethyl acetate using a $SiO_2$—$Pt_m Sn_{1-m}$ catalyst;

FIG. 1B is a graph of the productivity to ethanol and ethyl acetate of the catalyst of FIG. 1A;

FIG. 1C is a graph of the conversion of the acetic acid of the catalyst of FIG. 1A;

FIG. 2A is a graph of the selectivity to ethanol and ethyl acetate using a $SiO_2$—$Re_n Pd_{1-n}$ catalyst;

FIG. 2B is a graph of the productivity to ethanol and ethyl acetate of the catalyst of FIG. 2A;

FIG. 2C is a graph of the conversion of the acetic acid of the catalyst of FIG. 2A;

FIG. 6A is a graph of the conversion of the catalysts of Example 18;

FIG. 6B is a graph of the productivity of the catalysts of Example 18;

FIG. 6C is a graph of the selectivity at 250° C. of the catalysts of Example 18; and FIG. 6D is a graph of the selectivity at 275° C. of the catalysts of Example 18.

DETAILED DESCRIPTION OF THE INVENTION

Figures 3A, 3B:
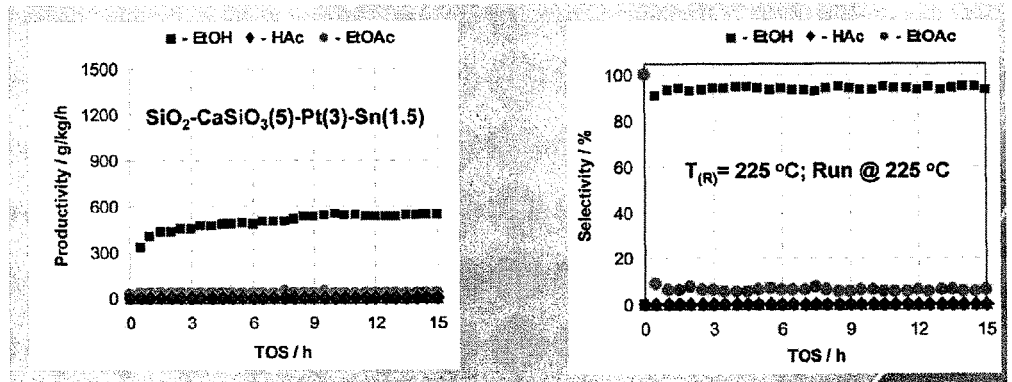
FIG. 3A is a graph of the productivity of a catalyst to ethanol at 15 hours of testing.
FIG. 3B is a graph of the selectivity of the catalyst of FIG. 3A to ethanol.

The present invention relates to processes for producing ethanol by hydrogenating acetic acid in the presence of a catalyst. The catalyst employed in the process comprises at least one metal, a silicaceous support, and at least one support modifier. The present invention also relates to the catalysts used in this process and processes for making the catalysts. The hydrogenation reaction may be represented as follows:

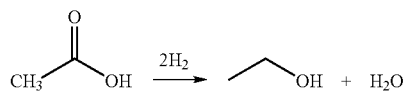

It has surprisingly and unexpectedly been discovered that the catalysts of the present invention provide high selectivities to ethoxylates, such as ethanol and ethyl acetate, and in particular to ethanol, when employed in the hydrogenation of acetic acid. Embodiments of the present invention beneficially may be used in industrial applications to produce ethanol on an economically feasible scale.

The catalyst of the invention comprises a first metal and optionally one or more of a second metal, a third metal or additional metals on the support. In this context, the numerical terms "first," "second," "third," etc., when used to modify the word "metal," are meant to indicate that the respective metals are different from one another. The total weight of all supported metals present in the catalyst preferably is from 0.1 to 25 wt. %, e.g., from 0.1 to 15 wt. %, or from 0.1 wt. % to 10 wt. %. For purposes of the present specification, unless otherwise indicated, weight percent is based on the total weight the catalyst including metal and support. The metal(s) in the catalyst may be present in the form of one or more metal oxides. For purposes of determining the weight percent of the metal(s) in the catalyst, the weight of any oxygen that is bound to the metal is ignored.

The first metal may be a Group IB, IIB, IIIB, IVB, VB, VIB, VIIB, or VIII transitional metal, a lanthanide metal, an actinide metal or a metal from any of Groups IIIA, IVA, VA, or VIA. In a preferred embodiment, the first metal is selected the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the availability of platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

Where the catalyst includes two or more metals, one metal may act as a promoter metal and the other metal is the main metal. For instance, with a platinum/tin catalyst, platinum may be considered to be the main metal and tin may be considered the promoter metal. For convenience, the present specification refers to the first metal as the primary catalyst and the second metal (and optional metals) as the promoter(s). This should not be taken as an indication of the underlying mechanism of the catalytic activity.

If the catalyst includes two or more metals, e.g., a first metal and a second metal, the first metal optionally is present in the catalyst in an amount from 0.1 to 10 wt. %, e.g., from 0.1 to 5 wt. %, or from 0.1 to 3 wt. %. The second metal preferably is present in an amount from 0.1 and 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary somewhat depending on the metals used in the catalyst. In some embodiments, the mole ratio of the first metal to the second metal preferably is from 10:1 to 1:10, e.g., from 4:1 to 1:4, from 2:1 to 1:2, from 1.5:1 to 1:1.5 or from 1.1:1 to 1:1.1. It has now surprisingly and unexpectedly been discovered that for platinum/tin catalysts, platinum to tin molar ratios on the order of from 0.4:0.6 to 0.6:0.4 (or about 1:1) are particularly preferred in order to form ethanol from acetic acid at high selectivity, conversion and productivity, as shown in FIGS. 1A, 1B and 1C. Selectivity to ethanol may be further improved by incorporating modified supports as described throughout the present specification.

Molar ratios other than 1:1 may be preferred for other catalysts. With rhenium/palladium catalysts, for example, higher ethanol selectivities may be achieved at higher rhenium loadings than palladium loadings. As shown in FIGS. 2A, 2B and 2C, preferred rhenium to palladium molar ratios for forming ethanol in terms of selectivity, conversion and production are on the order of 0.7:0.3 to 0.85:0.15, or about 0.75:0.25 (3:1). Again, selectivity to ethanol may be further improved by incorporating modified supports as described throughout the present specification.

In embodiments when the catalyst comprises a third metal, the third metal may be selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 and 4 wt. %, e.g., from 0.1 to 3 wt. %, or from 0.1 to 2 wt. %.

In one embodiment, the catalyst comprises a first metal and no additional metals (no second metal, etc.). In this embodiment, the first metal preferably is present in an amount from 0.1 to 10 wt. %. In another embodiment, the catalyst comprises a combination of two or more metals on a support.

Specific preferred metal compositions for various catalysts of this embodiment of the invention are provided below in Table 1. Where the catalyst comprises a first metal and a second metal, the first metal preferably is present in an amount from 0.1 to 5 wt. % and the second metal preferably is present in an amount from 0.1 to 5 wt. %. Where the catalyst comprises a first metal, a second metal and a third metal, the first metal preferably is present in an amount from 0.1 to 5 wt. %, the second metal preferably is present in an amount from 0.1 to 5 wt. %, and the third metal preferably is present in an amount from 0.1 to 2 wt. %. In one exemplary embodiment, the first metal is platinum and is present in an amount from 0.1 to 5 wt. %, the second metal is present in an amount from 0.1 to 5 wt. %, and the third metal, if present, preferably is present in an amount from 0.05 to 2 wt. %.

TABLE 1

EXEMPLARY METAL COMBINATIONS FOR CATALYSTS

| First Metal | Second Metal | Third Metal |
| --- | --- | --- |
| Cu | Ag | |
| Cu | Cr | |
| Cu | V | |
| Cu | W | |
| Cu | Zn | |
| Ni | Au | |
| Ni | Re | |
| Ni | V | |
| Ni | W | |
| Pd | Co | |
| Pd | Cr | |
| Pd | Cu | |
| Pd | Fe | |
| Pd | La | |
| Pd | Mo | |
| Pd | Ni | |
| Pd | Re | |
| Pd | Sn | |
| Pd | V | |
| Pd | W | |
| Pt | Co | |
| Pt | Cr | |
| Pt | Cu | |
| Pt | Fe | |
| Pt | Mo | |
| Pt | Sn | |
| Pt | Sn | Co |
| Pt | Sn | Re |
| Pt | Sn | Ru |
| Pt | Sn | Pd |
| Rh | Cu | |
| Rh | Ni | |
| Ru | Co | |
| Ru | Cr | |
| Ru | Cu | |
| Ru | Fe | |
| Ru | La | |
| Ru | Mo | |
| Ru | Ni | |
| Ru | Sn | |

Depending primarily on how the catalyst is manufactured, the metals of the catalysts of the present invention may be dispersed throughout the support, coated on the outer surface of the support (egg shell) or decorated on the surface of the support.

In addition to one or more metals, the catalysts of the present invention further comprise a modified support, meaning a support that includes a support material and a support modifier, which adjusts the acidity of the support material. For example, the acid sites, e.g. Brønsted acid sites, on the support material may be adjusted by the support modifier to favor selectivity to ethanol during the hydrogenation of acetic acid. The acidity of the support material may be adjusted by reducing the number or reducing the availability of Brønsted acid sites on the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. It has now been discovered that in addition to the metal precursors and preparation conditions employed, metal-support interactions may have a strong impact on selectivity to ethanol. In particular, the use of modified supports that adjust the acidity of the support to make the support less acidic or more basic surprisingly and unexpectedly has now been demonstrated to favor formation of ethanol over other hydrogenation products.

As will be appreciated by those of ordinary skill in the art, support materials are selected such that the catalyst system is suitably active, selective and robust under the process conditions employed for the formation of ethanol. Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica and mixtures thereof. Other supports may be used in some embodiments of the present invention, including without limitation, iron oxide, alumina, titania, zirconia, magnesium oxide, carbon, graphite, high surface area graphitized carbon, activated carbons, and mixtures thereof.

In preferred embodiments, the support comprises a basic support modifier having a low volatility or that is non-volatile. Low volatility modifiers have a rate of loss that is low enough such that the acidity of the support modifier is not reversed during the life of the catalyst. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used in embodiments of the present invention. Preferably, the support modifier is selected from the group consisting of oxides and metasilicates of any of sodium, potassium, magnesium, calcium, scandium, yttrium, and zinc, and mixtures of any of the foregoing. Preferably, the support modifier is a calcium silicate, more preferably calcium metasilicate ($CaSiO_3$). If the support modifier comprises calcium metasilicate, it is preferred that at least a portion of the calcium metasilicate is in crystalline form.

The total weight of the modified support, which includes the support material and the support modifier, based on the total weight of the catalyst, preferably is from 75 wt. % to 99.9 wt. %, e.g., from 78 wt. % to 97 wt. %, or from 80 wt. % to 95 wt. %. The support modifier preferably is provided in an amount sufficient to adjust the acidity, e.g., by reducing the number or reducing the availability of active Brønsted acid sites, and more preferably to ensure that the surface of the support is substantially free of active Brønsted acid sites. In preferred embodiments, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst. In preferred embodiments, the support material is present in an amount from 25 wt. % to 99 wt. %, e.g., from 30 wt. % to 97 wt. % or from 35 wt. % to 95 wt. %.

In one embodiment, the support material is a silicaceous support material selected from the group consisting of silica, silica/alumina, a Group IIA silicate such as calcium metasilicate, pyrogenic silica, high purity silica and mixtures thereof. In the case where silica is used as the silicaceous support, it is beneficial to ensure that the amount of aluminum, which is a common contaminant for silica, is low, preferably under 1 wt. %, e.g., under 0.5 wt. % or under 0.3 wt. %, based on the total weight of the modified support. In this regard, pyrogenic silica is preferred as it commonly is available in purities exceeding 99.7 wt. %. High purity silica, as used throughout the application, refers to silica in which acidic contaminants such as aluminum are present, if at all, at levels of less than 0.3 wt. %, e.g., less than 0.2 wt. % or less than 0.1 wt. %. When calcium metasilicate is used as a support modifier, it is not necessary to be quite as strict about the purity of the silica used as the support material although aluminum remains undesirable and will not normally be added intentionally. The aluminum content of such silica, for example, may be less than 10 wt. %, e.g., less than 5 wt. % or less than 3 wt. %. In cases where the support comprises a support modifier in the range of from 2 wt. % to 10 wt. %, larger amount of acidic impurities, such as aluminum, can be tolerated so long as they are substantially counter-balanced by an appropriate amount of a support modifier.

The surface area of the silicaceous support material, e.g., silica, preferably is at least about 50 m$^2$/g, e.g., at least about 100 m$^2$/g, at least about 150 m$^2$/g, at least about 200 m$^2$/g or most preferably at least about 250 m$^2$/g. In terms of ranges, the silicaceous support material preferably has a surface area of from 50 to 600 m$^2$/g, e.g., from 100 to 500 m$^2$/g or from 100 to 300 m$^2$/g. High surface area silica, as used throughout the application, refers to silica having a surface area of at least about 250 m$^2$/g. For purposes of the present specification, surface area refers to BET nitrogen surface area, meaning the surface area as determined by ASTM D6556-04, the entirety of which is incorporated herein by reference.

The silicaceous support material also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 cm$^3$/g, e.g., from 0.7 to 1.5 cm$^3$/g or from about 0.8 to 1.3 cm$^3$/g, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density of from 0.1 to 1.0 g/cm$^3$, e.g., from 0.2 to 0.9 g/cm$^3$ or from 0.5 to 0.8 g/cm$^3$. In terms of size, the silica support material preferably has an average particle size, e.g., meaning the diameter for spherical particles or equivalent spherical diameter for non-spherical particles, of from 0.01 to 1.0 cm, e.g., from 0.1 to 0.5 cm or from 0.2 to 0.4 cm. Since the one or more metal(s) that are disposed on or within the modified support are generally very small in size, they should not substantially impact the size of the overall catalyst particles. Thus, the above particle sizes generally apply to both the size of the modified supports as well as to the final catalyst particles.

A preferred silica support material is SS61138 High Surface Area (HSA) Silica Catalyst Carrier from Saint Gobain NorPro. The Saint-Gobain NorPro SS61138 silica contains approximately 95 wt. % high surface area silica; a surface area of about 250 m$^2$/g; a median pore diameter of about 12 nm; an average pore volume of about 1.0 cm$^3$/g as measured by mercury intrusion porosimetry and a packing density of about 0.352 g/cm$^3$ (22 lb/ft$^3$).

A preferred silica/alumina support material is KA-160 (Sud Chemie) silica spheres having a nominal diameter of about 5 mm, a density of about 0.562 g/ml, in absorptivity of about 0.583 g H$_2$O/g support, a surface area of about 160 to 175 m$^2$/g, and a pore volume of about 0.68 ml/g.

In embodiments where substantially pure ethanol is to be produced at high selectivity, as indicated above, controlling the Brønsted acidity of the support material by incorporating a support modifier can be quite beneficial. One possible byproduct of the hydrogenation of acetic acid is ethyl acetate. According to the present invention, the support preferably includes a support modifier that is effective to suppress production of ethyl acetate, rendering the catalyst composition highly selective to ethanol. Thus, the catalyst composition preferably has a low selectivity toward conversion of acetic acid to ethyl acetate and highly undesirable by-products such as alkanes. The acidity of the support preferably is controlled such that less than 4%, preferably less than 2% and most preferably less than about 1% of the acetic acid is converted to methane, ethane and carbon dioxide. In addition, the acidity of the support may be controlled by using a pyrogenic silica or high purity silica as discussed above.

In one embodiment, the modified support comprises a support material and calcium metasilicate as support modifier in an amount effective to balance Brønsted acid sites resulting, for example, from residual alumina in the silica. Preferably, the calcium metasilicate is present in an amount from 1 wt. % to 10 wt. %, based on the total weight of the catalyst, in order to ensure that the support is essentially neutral or basic in character.

As the support modifier, e.g., calcium metasilicate, may tend to have a lower surface area than the support material, e.g., silicaceous support material, in one embodiment the support material comprises a silicaceous support material that includes at least about 80 wt. %, e.g., at least about 85 wt. % or at least about 90 wt. %, high surface area silica in order to counteract this effect of including a support modifier.

In another aspect, the catalyst composition may be represented by the formula:

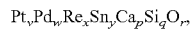

wherein: (i) the ratio of v:y is between 3:2 and 2:3; and/or (ii) the ratio of w:x is between 1:3 and 1:5. Thus, in this embodiment, the catalyst may comprise (i) platinum and tin; (ii) palladium and rhenium; or (iii) platinum, tin, palladium and rhenium. p and q preferably are selected such that p:q is from 1:20 to 1:200 with r being selected to satisfy valence requirements and v and w being selected such that:

$$0.005 \leq \frac{(3.25v + 1.75w)}{q} \leq 0.05$$

In this aspect, the process conditions and values of v, w, x, y, p, q, and r are preferably chosen such that at least 70% of the acetic acid, e.g., at least 80% or at least 90%, that is converted is converted to a compound selected from the group consisting of ethanol and ethyl acetate while less than 4% of the acetic acid is converted to alkanes. More preferably, the process conditions and values of v, w, x, y, p, q, and r are preferably chosen such that at least 70% of the acetic acid, e.g., at least 80% or at least 90%, that is converted is converted to ethanol, while less than 4% of the acetic acid is converted to alkanes. In many embodiments of the present invention, p is selected, in view of any minor impurities present, to ensure that the surface of the support is essentially free of active Brønsted acid sites.

In another aspect, the composition of the catalyst comprises:

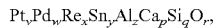

wherein: (i) v and y are between 3:2 and 2:3; and/or (ii) w and x are between 1:3 and 1:5. p and z and the relative locations of aluminum and calcium atoms present preferably are controlled such that Brønsted acid sites present upon the surface thereof are balanced by the support modifier, e.g., calcium metasilicate; p and q are selected such that p:q is from 1:20 to 1:200 with r being selected to satisfy valence requirements and v and w are selected such that:

$$0.005 \leq \frac{(3.25v + 1.75w)}{q} \leq 0.05$$

Preferably, in this aspect, the catalyst has a surface area of at least about 100 m²/g, e.g., at least about 150 m²/g, at least about 200 m²/g or most preferably at least about 250 m²/g, and z and p≧z. In many embodiments of the present invention, p is selected, in view of any minor impurities present, to also ensure that the surface of the support is substantially free of active Brønsted acid sites which seem to facilitate conversion of ethanol into ethyl acetate. Thus, as with the previous embodiment, the process conditions and values of v, w, x, y, p, q, and r preferably are chosen such that at least 70% of the acetic acid, e.g., at least 80% or at least 90%, that is converted is converted to ethanol, while less than 4% of the acetic acid is converted to alkanes.

Accordingly, without being bound by theory, modification and stabilization of oxidic support materials for the catalysts of the present invention by incorporation of non-volatile support modifiers having either the effect of: counteracting acid sites present upon the support surface or the effect of thermally stabilizing the surface makes it possible to achieve desirable improvements in selectivity to ethanol, prolonged catalyst life, or both. In general, support modifiers based on oxides in their most stable valence state will have low vapor pressures and thus have low volatility or are rather non-volatile. Accordingly, it is preferred that the support modifiers are provided in amounts sufficient to: (i) counteract acidic sites present on the surface of the support material; (ii) impart resistance to shape change under hydrogenation temperatures; or (iii) both. Without being bound by theory, imparting resistance to shape change refers to imparting resistance, for example, to sintering, grain growth, grain boundary migration, migration of defects and dislocations, plastic deformation and/or other temperature induced changes in microstructure.

Catalysts of the present invention are particulate catalysts in the sense that, rather than being impregnated in a wash coat onto a monolithic carrier similar to automotive catalysts and diesel soot trap devices, the catalysts of the invention preferably are formed into particles, sometimes also referred to as beads or pellets, having any of a variety of shapes and the catalytic metals are provided to the reaction zone by placing a large number of these shaped catalysts in the reactor. Commonly encountered shapes include extrudates of arbitrary cross-section taking the form of a generalized cylinder in the sense that the generators defining the surface of the extrudate are parallel lines. As indicated above, any convenient particle shape including pellets, extrudates, spheres, spray dried microspheres, rings, pentarings, trilobes, quadrilobes and multi-lobal shapes may be used, although cylindrical pellets are preferred. Typically, the shapes are chosen empirically based upon perceived ability to contact the vapor phase with the catalytic agents effectively.

One advantage of catalysts of the present invention is the stability or activity of the catalyst for producing ethanol. Accordingly, it can be appreciated that the catalysts of the present invention are fully capable of being used in commercial scale industrial applications for hydrogenation of acetic acid, particularly in the production of ethanol. In particular, it is possible to achieve such a degree of stability such that catalyst activity will have rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

In one embodiment, when the catalyst support comprises high purity silica, with calcium metasilicate as a support modifier, the catalyst activity may extend or stabilize, the productivity and selectivity of the catalyst for prolonged periods extending into over one week, over two weeks, and even months, of commercially viable operation in the presence of acetic acid vapor at temperatures of 125° C. to 350° C. at space velocities of greater than 2500 hr⁻¹.

The catalyst compositions of the invention preferably are formed through metal impregnation of the modified support, although other processes such as chemical vapor deposition may also be employed. Before the metals are impregnated, it typically is desired to form the modified support, for example, through a step of impregnating the support material with the support modifier. A precursor to the support modifier, such as an acetate or a nitrate, may be used. In one aspect, the support modifier, e.g., CaSiO₃, is added to the support material, e.g., SiO₂. For example, an aqueous suspension of the support modifier may be formed by adding the solid support modifier to deionized water, followed by the addition of colloidal support material thereto. The resulting mixture may be stirred and added to additional support material using, for example, incipient wetness techniques in which the support modifier is added to a support material having the same pore volume as the volume of the support modifier solution. Capillary action then draws the support modifier into the pores in the support material. The modified support can then be formed by drying and calcining to drive off water and any volatile components within the support modifier solution and depositing the support modifier on the support material. Drying may occur, for example, at a temperature of from 50° C. to 300° C., e.g., from 100° C. to 200° C. or about 120° C., optionally for a period of from 1 to 24 hours, e.g., from 3 to 15 hours or from 6 to 12 hours. Once formed, the modified supports may be shaped into particles having the desired size distribution, e.g., to form particles having an average particle size in the range of from 0.2 to 0.4 cm. The supports may be extruded, pelletized, tabletized, pressed, crushed or sieved to the desired size distribution. Any of the known methods to shape the support materials into desired size distribution can be employed. Calcining of the shaped modified support may occur, for example, at a temperature of from 250° C. to 800° C., e.g., from 300 to 700° C. or about 500° C., optionally for a period of from 1 to 12 hours, e.g., from 2 to 10 hours, from 4 to 8 hours or about 6 hours.

In a preferred method of preparing the catalyst, the metals are impregnated onto the modified support. A precursor of the first metal (first metal precursor) preferably is used in the metal impregnation step, such as a water soluble compound or water dispersible compound/complex that includes the first metal of interest. Depending on the metal precursor employed, the use of a solvent, such as water, glacial acetic acid or an organic solvent, may be preferred. The second metal also preferably is impregnated into the modified support from a second metal precursor. If desired, a third metal or third metal precursor may also be impregnated into the modified support.

Impregnation occurs by adding, optionally drop wise, either or both the first metal precursor and/or the second metal precursor and/or additional metal precursors, preferably in suspension or solution, to the dry modified support. The resulting mixture may then be heated, e.g., optionally under vacuum, in order to remove the solvent. Additional drying and calcining may then be performed, optionally with ramped heating to form the final catalyst composition. Upon heating and/or the application of vacuum, the metal(s) of the metal precursor(s) preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the first and second metals (and optional additional metals) into the modified support may occur simultaneously (co-impregnation) or sequentially. In simultaneous impregnation, the first and second metal precursors (and optionally additional metal precursors) are mixed together and added to the modified support together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the first and second metal precursors in the event the two precursors are incompatible with the desired solvent, e.g., water.

In sequential impregnation, the first metal precursor is first added to the modified support followed by drying and calcining, and the resulting material is then impregnated with the second metal precursor followed by an additional drying and calcining step to form the final catalyst composition. Additional metal precursors (e.g., a third metal precursor) may be added either with the first and/or second metal precursor or an a separate third impregnation step, followed by drying and calcination. Of course, combinations of sequential and simultaneous impregnation may be employed if desired.

Suitable metal precursors include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, and sodium platinum chloride. Generally, both from the point of view of economics and environmental aspects, aqueous solutions of soluble compounds of platinum are preferred. In one embodiment, the first metal precursor is not a metal halide and is substantially free of metal halides. Without being bound to theory, such non-(metal halide) precursors are believed to increase selectivity to ethanol. A particularly preferred precursor to platinum is platinum ammonium nitrate, $Pt(NH_3)_4(NO_4)_2$.

In one aspect, the "promoter" metal or metal precursor is first added to the modified support, followed by the "main" or "primary" metal or metal precursor. Of course the reverse order of addition is also possible. Exemplary precursors for promoter metals include metal halides, amine solubilized metal hydroxides, metal nitrates or metal oxalates. As indicated above, in the sequential embodiment, each impregnation step preferably is followed by drying and calcination. In the case of promoted bimetallic catalysts as described above, a sequential impregnation may be used, starting with the addition of the promoter metal followed by a second impregnation step involving co-impregnation of the two principal metals, e.g., Pt and Sn.

As an example, $PtSn/CaSiO_3$ on $SiO_2$ may be prepared by a first impregnation of $CaSiO_3$ onto the $SiO_2$, followed by the co-impregnation with $Pt(NH_3)_4(NO_4)_2$ and $Sn(AcO)_2$. Again, each impregnation step may be followed by drying and calcination steps. In most cases, the impregnation may be carried out using metal nitrate solutions. However, various other soluble salts, which upon calcination release metal ions, can also be used. Examples of other suitable metal salts for impregnation include, metal acids, such as perrhenic acid solution, metal oxalates, and the like. In those cases where substantially pure ethanol is to be produced, it is generally preferable to avoid the use of halogenated precursors for the platinum group metals, using the nitrogenous amine and/or nitrate based precursors instead.

The process of hydrogenating acetic acid to form ethanol according to one embodiment of the invention may be conducted in a variety of configurations using a fixed bed reactor or a fluidized bed reactor as one of skill in the art will readily appreciate. In many embodiments of the present invention, an "adiabatic" reactor can be used; that is, there is little or no need for internal plumbing through the reaction zone to add or remove heat. Alternatively, a shell and tube reactor provided with a heat transfer medium can be used. In many cases, the reaction zone may be housed in a single vessel or in a series of vessels with heat exchangers therebetween. It is considered significant that acetic acid reduction processes using the catalysts of the present invention may be carried out in adiabatic reactors as this reactor configuration is typically far less capital intensive than tube and shell configurations.

Typically, the catalyst is employed in a fixed bed reactor, e.g., in the shape of an elongated pipe or tube where the reactants, typically in the vapor form, are passed over or through the catalyst. Other reactors, such as fluid or ebullient bed reactors, can be employed, if desired. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably the reaction is carried out in the vapor phase under the following conditions. The reaction temperature may the range from of 125° C. to 350° C., e.g., from 200° C. to 325° C., from 225° C. to about 300° C., or from 250° C. to about 300° C. The pressure may range from 10 KPa to 3000 KPa (about 0.1 to 30 atmospheres), e.g., from 50 KPa to 2300 KPa, or from 100 KPa to 1500 KPa. The reactants may be fed to the reactor at a gas hourly space velocities (GHSV) of greater than 500 $hr^{-1}$, e.g., greater than 1000 hr$^{-1}$, greater than 2500 hr$^{-1}$ and even greater than 5000 hr$^{-1}$. In terms of ranges the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 6500 hr$^{-1}$.

In another aspect of the process of this invention, the hydrogenation is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 6,500 hr$^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 4:1, e.g., greater than 5:1 or greater than 10:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The acetic acid may be vaporized at the reaction temperature, and then the vaporized acetic acid can be fed along with hydrogen in undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid.

In particular, using catalysts and processes of the present invention may achieve favorable conversion of acetic acid and favorable selectivity and productivity to ethanol. For purposes of the present invention, the term conversion refers to the amount of acetic acid in the feed that is convert to a compound other than acetic acid. Conversion is expressed as a mole percentage based on acetic acid in the feed.

The conversion of acetic acid (AcOH) is calculated from gas chromatography (GC) data using the following equation:

$$\text{AcOH } Conv. \text{ (\%)} = 100 * \frac{\text{mmol AcOH (feed stream)} - \text{mmol AcOH } (GC)}{\text{mmol AcOH (feed stream)}}$$

For purposes of the present invention, the conversion may be at least 10%, e.g., at least 20%, at least 40%, at least 50%, at least 60%, at least 70% or at least 80%. Although catalysts that have high conversions are desirable, such as at least 80% or at least 90%, a low conversion may be acceptable at high selectivity for ethanol. It is, of course, well understood that in many cases, it is possible to compensate for conversion by appropriate recycle streams or use of larger reactors, but it is more difficult to compensate for poor selectivity.

"Selectivity" is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Selectivity to ethanol (EtOH) is calculated from gas chromatography (GC) data using the following equation:

$$\text{EtOH } Sel. \text{ (\%)} = 100 * \frac{\text{mmol EtOH } (GC)}{\frac{\text{Total mmol } C(GC)}{2} - \text{mmol AcOH (feed stream)}}$$

wherein "Total mmol C (GC)" refers to total mmols of carbon from all of the products analyzed by gas chromatograph.

For purposes of the present invention, the selectivity to ethoxylates of the catalyst is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. In embodiments of the present invention is also desirable to have low selectivity to undesirable products, such as methane, ethane, and carbon dioxide. The selectivity to these undesirable products is less than 4%, e.g., less than 2% or less than 1%. Preferably, no detectable amounts of these undesirable products are formed during hydrogenation. In several embodiments of the present invention, formation of alkanes is low, usually under 2%, often under 1%, and in many cases under 0.5% of the acetic acid passed over the catalyst is converted to alkanes, which have little value other than as fuel.

Productivity refers to the grams of a specified product, e.g., ethanol, formed during the hydrogenation based on the kilogram of catalyst used per hour. In one embodiment of the present invention, a productivity of at least 200 grams of ethanol per kilogram catalyst per hour, e.g., at least 400 grams of ethanol or least 600 grams of ethanol, is preferred. In terms of ranges, the productivity preferably is from 200 to 3,000 grams of ethanol per kilogram catalyst per hour, e.g., from 400 to 2,500 or from 600 to 2,000.

Some catalysts of the present invention may achieve a conversion of acetic acid of at least 10%, a selectivity to ethanol of at least 80%, and a productivity of at least 200 g of ethanol per kg of catalyst per hour. A subset of catalysts of the invention may achieve a conversion of acetic acid of at least 50%, a selectivity to ethanol of at least 80%, a selectivity to undesirable compounds of less than 4%, and a productivity of at least 600 g of ethanol per kg of catalyst per hour.

In another embodiment, the invention is to a crude ethanol product formed by processes of the present invention. The crude ethanol product produced by the hydrogenation process of the present invention, before any subsequent processing, such as purification and separation, typically will comprise primarily unreacted acetic acid and ethanol. In some exemplary embodiments, the crude ethanol product comprises ethanol in an amount from 15 wt. % to 70 wt. %, e.g., from 20 wt. % to 50 wt. %, or from 25 wt % to 50 wt. %, based on the total weight of the crude ethanol product. Preferably, the crude ethanol product contains at least 22 wt. % ethanol, at least 28 wt. % ethanol or at least 44 wt. % ethanol. The crude ethanol product typically will further comprise unreacted acetic acid, depending on conversion, for example, in an amount from 0 to 80 wt %, e.g., from 5 to 80 wt %, from 20 to 70 wt. %, from 28 to 70 wt. % or from 44 to 65 wt. %. Since water is formed in the reaction process, water will also be present in the crude ethanol product, for example, in amounts ranging from 5 to 30 wt. %, e.g., from 10 to 30 wt. % or from 10 to 26 wt. %. Other components, such as, for example, esters, ethers, aldehydes, ketones, alkanes, and carbon dioxide, if detectable, collectively may be present in amounts less than 10 wt. %, e.g., less than 6 or less than 4 wt. %. In terms of ranges other components may be present in an amount from 0.1 to 10 wt. %, e.g., from 0.1 to 6 wt. %, or from 0.1 to 4 wt. %. Thus, exemplary crude ethanol compositional ranges in various embodiments of the invention are provided below in Table 2.

TABLE 2

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 15-70 | 15-70 | 20-50 | 25-50 |
| Acetic Acid | 5-80 | 20-70 | 28-70 | 44-65 |
| Water | 5-30 | 5-30 | 10-30 | 10-26 |
| Other | <10 | <10 | <6 | <4 |

In a preferred embodiment, the crude ethanol product is formed over a platinum/tin catalyst on a modified silica support, e.g., modified with CaSiO$_3$. Depending on the specific catalyst and process conditions employed, the crude ethanol product may have any of the compositions indicated below in Table 3.

TABLE 3

CRUDE ETHANOL PRODUCT COMPOSITIONS

| Component | Comp. A Conc. (wt. %) | Comp. B Conc. (wt. %) | Comp. C Conc. (wt. %) |
|---|---|---|---|
| Ethanol | 17 | 26 | 45 |
| Acetic Acid | 74 | 53 | 20 |
| Water | 7 | 13 | 25 |
| Other | 2 | 8 | 10 |

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation. As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352 to Vidalin, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, the process can also be used to make hydrogen which may be utilized in connection with this invention.

U.S. Pat. No. RE 35,377 to Steinberg et al., also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. See also, U.S. Pat. No. 5,821,111 to Grady et al., which discloses a process for converting waste biomass through gasification into synthesis gas as well as U.S. Pat. No. 6,685,754 to Kindig et al., the disclosures of which are incorporated herein by reference.

Alternatively, acetic acid in vapor form may be taken directly as crude product from the flash vessel of a methanol carbonylation unit of the class described in U.S. Pat. No. 6,657,078 to Scates et al., the entirety of which is incorporated herein by reference. The crude vapor product, for example, may be fed directly to the ethanol synthesis reaction zones of the present invention without the need for condensing the acetic acid and light ends or removing water, saving overall processing costs.

Ethanol, obtained from hydrogenation processes of the present invention, may be used in its own right as a fuel or subsequently converted to ethylene which is an important commodity feedstock as it can be converted to polyethylene, vinyl acetate and/or ethyl acetate or any of a wide variety of other chemical products. For example, ethylene can also be converted to numerous polymer and monomer products. The dehydration of ethanol to ethylene is shown below.

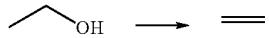

Any of known dehydration catalysts can be employed in to dehydrate ethanol, such as those described in copending applications U.S. application Ser. Nos. 12/221,137 and 12/221,138, the entire contents and disclosures of which are hereby incorporated by reference. A zeolite catalyst, for example, may be employed as the dehydration catalyst. While any zeolite having a pore diameter of at least about 0.6 nm can be used, preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

Ethanol may also be used as a fuel, in pharmaceutical products, cleansers, sanitizers, hydrogenation transport or consumption. Ethanol may also be used as a source material for making ethyl acetate, aldehydes, and higher alcohols, especially butanol. In addition, any ester, such as ethyl acetate, formed during the process of making ethanol according to the present invention may be further reacted with an acid catalyst to form additional ethanol as well as acetic acid, which may be recycled to the hydrogenation process.

The invention is described in detail below with reference to numerous embodiments for purposes of exemplification and illustration only. Modifications to particular embodiments within the spirit and scope of the present invention, set forth in the appended claims, will be readily apparent to those of skill in the art.

The following examples describe the procedures used for the preparation of various catalysts employed in the process of this invention.

EXAMPLES

Catalyst Preparations (General)

The catalyst supports were dried at 120° C. overnight under circulating air prior to use. All commercial supports (i.e., SiO$_2$, ZrO$_2$) were used as a 14/30 mesh, or in its original shape (1/16 inch or 1/8 inch pellets) unless mentioned otherwise. Powdered materials (i.e., $CaSiO_3$) were pelletized, crushed and sieved after the metals had been added. The individual catalyst preparations are described in detail below.

Example 1

$SiO_2$—$CaSiO_3$(5)-Pt(3)-Sn(1.8) Catalyst

The catalyst was prepared by first adding $CaSiO_3$ (Aldrich) to the $SiO_2$ catalyst support, followed by the addition of Pt/Sn. First, an aqueous suspension of $CaSiO_3$ ($\leq$200 mesh) was prepared by adding 0.52 g of the solid to 13 ml of deionized $H_2O$, followed by the addition of 1.0 ml of colloidal $SiO_2$ (15 wt. % solution, NALCO). The suspension was stirred for 2 hours at room temperature and then added to 10.0 g of $SiO_2$ catalyst support (14/30 mesh) using incipient wetness technique. After standing for 2 hours, the material was evaporated to dryness, followed by drying at 120° C. overnight under circulating air and calcination at 500° C. for 6 hours. All of the $SiO_2$—$CaSiO_3$ material was then used for Pt/Sn metal impregnation.

The catalysts were prepared by first adding $Sn(OAc)_2$ (tin acetate, $Sn(OAc)_2$ from Aldrich) (0.4104 g, 1.73 mmol) to a vial containing 6.75 ml of 1:1 diluted glacial acetic acid (Fisher). The mixture was stirred for 15 min at room temperature, and then, 0.6711 g (1.73 mmol) of solid $Pt(NH_3)_4(NO_3)_2$ (Aldrich) were added. The mixture was stirred for another 15 min at room temperature, and then added drop wise to 5.0 g of $SiO_2$—$CaSiO_3$ support, in a 100 ml round-bottomed flask. The metal solution was stirred continuously until all of the Pt/Sn mixture had been added to the $SiO_2$—$CaSiO_3$ support while rotating the flask after every addition of metal solution. After completing the addition of the metal solution, the flask containing the impregnated catalyst was left standing at room temperature for two hours. The flask was then attached to a rotor evaporator (bath temperature 80° C.), and evacuated until dried while slowly rotating the flask. The material was then dried further overnight at 120° C., and then calcined using the following temperature program: 25→160° C./ramp 5.0 deg/min; hold for 2.0 hours; 160→500° C./ramp 2.0 deg/min; hold for 4 hours. Yield: 11.21 g of dark grey material.

Example 2

KA160-$CaSiO_3$(8)-Pt(3)-Sn(1.8)

The material was prepared by first adding $CaSiO_3$ to the KA160 catalyst support ($SiO_2$-(0.05) $Al_2O_3$, Sud Chemie, 14/30 mesh), followed by the addition of Pt/Sn. First, an aqueous suspension of $CaSiO_3$ ($\leq$200 mesh) was prepared by adding 0.42 g of the solid to 3.85 ml of deionized $H_2O$, followed by the addition of 0.8 ml of colloidal $SiO_2$ (15 wt. % solution, NALCO). The suspension was stirred for 2 hours at room temperature and then added to 5.0 g of KA160 catalyst support (14/30 mesh) using incipient wetness technique. After standing for 2 hours, the material was evaporated to dryness, followed by drying at 120° C. overnight under circulating air and calcinations at 500° C. for 6 hours. All of the KA160-$CaSiO_3$ material was then used for Pt/Sn metal impregnation.

The catalysts were prepared by first adding $Sn(OAc)_2$ (tin acetate, $Sn(OAc)_2$ from Aldrich) (0.2040 g, 0.86 mmol) to a vial containing 6.75 ml of 1:1 diluted glacial acetic acid (Fisher). The mixture was stirred for 15 min at room temperature, and then, 0.3350 g (0.86 mmol) of solid $Pt(NH_3)_4(NO_3)_2$ (Aldrich) were added. The mixture was stirred for another 15 min at room temperature, and then added drop wise to 5.0 g of $SiO_2$—$CaSiO_3$ support, in a 100 ml round-bottomed flask. After completing the addition of the metal solution, the flask containing the impregnated catalyst was left standing at room temperature for two hours. The flask was then attached to a rotor evaporator (bath temperature 80° C.), and evacuated until dried while slowly rotating the flask. The material was then dried further overnight at 120° C., and then calcined using the following temperature program: 25→160° C./ramp 5.0 deg/min; hold for 2.0 hours; 160→500° C./ramp 2.0 deg/min; hold for 4 hours. Yield: 5.19 g of tan-colored material.

Example 3

$SiO_2$—$CaSiO_3$(2.5)-Pt(1.5)-Sn(0.9)

This catalyst was prepared in the same manner as Example 1, with the following starting materials: 0.26 g of $CaSiO_3$ as a support modifier; 0.5 ml of colloidal $SiO_2$ (15 wt. % solution, NALCO), 0.3355 g (0.86 mmol) of $Pt(NH_3)_4(NO_3)_2$; and 0.2052 g (0.86 mmol) of $Sn(OAc)_2$. Yield: 10.90 g of dark grey material.

Example 4

$SiO_2$+$MgSiO_3$—Pt(1.0)-Sn(1.0)

This catalyst was prepared in the same manner as Example 1, with the following starting materials: 0.69 g of Mg(AcO) as a support modifier; 1.3 g of colloidal $SiO_2$ (15 wt. % solution, NALCO), 0.2680 g (0.86 mmol) of $Pt(NH_3)_4(NO_3)_2$; and 0.1640 g (0.86 mmol) of $Sn(OAc)_2$. Yield: 8.35 g. The $SiO_2$ support was impregnated with a solution of Mg(AcO) and colloidal $SiO_2$. The support was dried and then calcined to 700° C.

Example 5

$SiO_2$—$CaSiO_3$(5)-Re(4.5)-Pd(1)

The $SiO_2$—$CaSiO_3$(5) modified catalyst support was prepared as described in Example 1. The Re/Pd catalyst was prepared then by impregnating the $SiO_2$—$CaSiO_3$(5) (1/16 inch extrudates) with an aqueous solution containing $NH_4ReO_4$ and $Pd(NO_3)_2$. The metal solutions were prepared by first adding $NH_4ReO_4$ (0.7237 g, 2.70 mmol) to a vial containing 12.0 ml of deionized $H_2O$. The mixture was stirred for 15 min at room temperature, and 0.1756 g (0.76 mmol) of solid $Pd(NO_3)_2$ was then added. The mixture was stirred for another 15 min at room temperature, and then added drop wise to 10.0 g of dry $SiO_2$-(0.05)$CaSiO_3$ catalyst support in a 100 ml round-bottomed flask. After completing the addition of the metal solution, the flask containing the impregnated catalyst was left standing at room temperature for two hours. All other manipulations (drying, calcination) were carried out as described in Example 1. Yield: 10.9 g of brown material.

Example 6

$SiO_2$—ZnO(5)-Pt(1)-Sn(1)

Powdered and meshed high surface area silica NPSG SS61138 (100 g) of uniform particle size distribution of about 0.2 mm was dried at 120° C. in a circulating air oven atmosphere overnight and then cooled to room temperature. To this was added a solution of zinc nitrate hexahydrate. The resulting slurry was dried in an oven gradually heated to 110° C. (>2 hours, 10° C./min.) then calcined. To this was added a solution of platinum nitrate (Chempur) in distilled water and a solution of tin oxalate (Alfa Aesar) (1.74 g) in dilute nitric acid (1N, 8.5 ml) The resulting slurry was dried in an oven gradually heated to 110° C. (>2 hours, 10° C./min.). The impregnated catalyst mixture was then calcined at 500° C. (6 hours, 1° C./min).

In addition, the following comparative catalysts were also prepared.

Example 7

Comparative $TiO_2$—$CaSiO_3$(5)-Pt(3)-Sn(1.8). The material was prepared by first adding $CaSiO_3$ to the $TiO_2$ catalyst (Anatase, 14/30 mesh) support, followed by the addition of Pt/Sn as described in Example 1. First, an aqueous suspension of $CaSiO_3$ ($\leqq$200 mesh) was prepared by adding 0.52 g of the solid to 7.0 ml of deionized $H_2O$, followed by the addition of 1.0 ml of colloidal $SiO_2$ (15 wt. % solution, NALCO). The suspension was stirred for 2 h at room temperature and then added to 10.0 g of $TiO_2$ catalyst support (14/30 mesh) using incipient wetness technique. After standing for 2 hours, the material was evaporated to dryness, followed by drying at 120° C. overnight under circulating air and calcination at 500° C. for 6 hours. All of the $TiO_2$—$CaSiO_3$ material was then used for Pt/Sn metal impregnation using 0.6711 g (1.73 mmol) of $Pt(NH_3)_4(NO_3)_2$ and 0.4104 g (1.73 mmol) of $Sn(OAc)_2$ following the procedure described in Example 1. Yield: 11.5 g of light grey material.

Example 8

Comparative

Sn(0.5) on High Purity Low Surface Area Silica. Powdered and meshed high purity low surface area silica (100 g) of uniform particle size distribution of about 0.2 mm was dried at 120° C. in an oven under nitrogen atmosphere overnight and then cooled to room temperature. To this was added a solution of tin oxalate (Alfa Aesar) (1.74 g) in dilute nitric acid (1 N, 8.5 ml). The resulting slurry was dried in an oven gradually heated to 110° C. (>2 hours, 10° C./min.). The impregnated catalyst mixture was then calcined at 500° C. (6 hours, 1° C./min).

Example 9

Comparative

Pt(2)-Sn(2) on High Surface Area Silica. Powdered and meshed high surface area silica NPSG SS61138 (100 g) of uniform particle size distribution of about 0.2 mm was dried at 120° C. in a circulating air oven atmosphere overnight and then cooled to room temperature. To this was added a solution of nitrate hexahydrate (Chempur). The resulting slurry was dried in an oven gradually heated to 110° C. (>2 hours, 10° C./min.) then calcined. To this was added a solution of platinum nitrate (Chempur) in distilled water and a solution of tin oxalate (Alfa Aesar) in dilute nitric acid. The resulting slurry was dried in an oven gradually heated to 110° C. (>2 hours, 10° C./min.). The impregnated catalyst mixture was then calcined at 500° C. (6 hours, 1° C./min).

Example 10

Comparative

KA160-Pt(3)-Sn(1.8). The material was prepared by incipient wetness impregnation of KA160 catalyst support ($SiO_2$-(0.05)$Al_2O_3$, Sud Chemie, 14/30 mesh) as described in Example 16. The metal solutions were prepared by first adding $Sn(OAc)_2$ (0.2040 g, 0.86 mmol) to a vial containing 4.75 ml of 1:1 diluted glacial acetic acid. The mixture was stirred for 15 min at room temperature, and then, 0.3350 g (0.86 mmol) of solid $Pt(NH_3)_4(NO_3)_2$ were added. The mixture was stirred for another 15 min at room temperature, and then added drop wise to 5.0 g of dry KA160 catalyst support (14/30 mesh) in a 100 ml round-bottomed flask. All other manipulations, drying and calcination was carried out as described in Example 16. Yield: 5.23 g of tan-colored material.

Example 11

Comparative $SiO_2$—$SnO_2$(5)-Pt(1)-Zn(1). Powdered and meshed high surface area silica NPSG SS61138 (100 g) of uniform particle size distribution of about 0.2 mm was dried at 120° C. in a circulating air oven atmosphere overnight and then cooled to room temperature. To this was added a solution of tin acetate ($Sn(OAc)_2$). The resulting slurry was dried in an oven gradually heated to 110° C. (>2 hours, 10° C./min.) then calcined. To this was added a solution of platinum nitrate (Chempur) in distilled water and a solution of tin oxalate (Alfa Aesar) in dilute nitric acid The resulting slurry was dried in an oven gradually heated to 110° C. (>2 hours, 10° C./min.). The impregnated catalyst mixture was then calcined at 500° C. (6 hours, 1° C./min).

Example 12

Comparative $SiO_2$—$TiO_2$(10)-Pt(3)-Sn(1.8). The $TiO_2$-modified silica support was prepared as follows. A solution of 4.15 g (14.6 mmol) of $Ti\{OCH(CH_3)_2\}_4$ in 2-propanol (14 ml) was added dropwise to 10.0 g of $SiO_2$ catalyst support (1/16 inch extrudates) in a 100 ml round-bottomed flask. The flask was left standing for two hours at room temperature, and then evacuated to dryness using a rotor evaporator (bath temperature 80° C.). Next, 20 ml of deionized $H_2O$ was slowly added to the flask, and the material was left standing for 15 min. The resulting water/2-propanol was then removed by filtration, and the addition of $H_2O$ was repeated two more times. The final material was dried at 120° C. overnight under circulation air, followed by calcination at 500° C. for 6 hours. All of the $SiO_2$—$TiO_2$ material was then used for Pt/Sn metal impregnation using 0.6711 g (1.73 mmol) of $Pt(NH_3)_4(NO_3)_2$ and 0.4104 g (1.73 mmol) of $Sn(OAc)_2$ following the procedure described above for Example 1. Yield: 11.98 g of dark grey 1/16 inch extrudates.

Example 13

Comparative $SiO_2$—$WO_3$(10)-Pt(3)-Sn(1.8). The $WO_3$-modified silica support was prepared as follows. A solution of 1.24 g (0.42 mmol) of $(NH_4)_6H_2W_{12}O_{40}\cdot nH_2O$, (AMT) in deionized $H_2O$ (14 ml) was added dropwise to 10.0 g of $SiO_2$ NPSGSS 61138 catalyst support (SA=250 $m^2$/g, 1/16 inch extrudates) in a 100 ml round-bottomed flask. The flask was left standing for two hours at room temperature, and then evacuated to dryness using a rotor evaporator (bath temperature 80° C.). The resulting material was dried at 120° C. overnight under circulation air, followed by calcination at 500° C. for 6 hours. All of the (light yellow) SiO$_2$—WO$_3$ material was then used for Pt/Sn metal impregnation using 0.6711 g (1.73 mmol) of Pt(NH$_3$)$_4$(NO$_3$)$_2$ and 0.4104 g (1.73 mmol) of Sn(OAc)$_2$ following the procedure described above for Example 1. Yield: 12.10 g of dark grey 1/16 inch extrudates.

Example 14

Hydrogenation of Acetic Acid Over Catalysts from Examples 1-13 and Gas Chromatographic (GC) Analysis of the Crude Ethanol Product Catalyst of Examples 1-13 were tested to determine the selectivity and productivity to ethanol as shown in Table 4.

The reaction feed liquid of acetic acid was evaporated and charged to the reactor along with hydrogen and helium as a carrier gas with an average combined gas hourly space velocity (GHSV), temperature, and pressure as indicated in Table 4. The feed stream contained a mole ratio hydrogen to acetic acid as indicated in Table 4.

The analysis of the products (crude ethanol composition) was carried out by online GC. A three channel compact GC equipped with one flame ionization detector (FID) and 2 thermal conducting detectors (TCDs) was used to analyze the reactants and products. The front channel was equipped with an FID and a CP-Sil 5 (20 m)+WaxFFap (5 m) column and was used to quantify: Acetaldehyde; Ethanol; Acetone; Methyl acetate; Vinyl acetate; Ethyl acetate; Acetic acid; Ethylene glycol diacetate; Ethylene glycol; Ethylidene diacetate; and Paraldehyde. The middle channel was equipped with a TCD and Porabond Q column and was used to quantify: CO$_2$; ethylene; and ethane. The back channel was equipped with a TCD and Molsieve 5A column and was used to quantify: Helium; Hydrogen; Nitrogen; Methane; and Carbon monoxide.

Prior to reactions, the retention times of the different components were determined by spiking with individual compounds and the GCs were calibrated either with a calibration gas of known composition or with liquid solutions of known compositions. This allowed the determination of the response factors for the various components.

Example 15

Catalyst Stability (15 Hours)

Vaporized acetic acid and hydrogen were passed over a hydrogenation catalyst of the present invention comprising 3 wt. % Pt, 1.5 wt. % Sn and 5 wt % CaSiO$_3$, as a promoter on high purity, high surface area silica having a surface area of approximately 250 m$^2$/g at a molar ratio of hydrogen to acetic acid of about 5:1 (feed rate of 0.09 g/min HOAc; 160 sccm/min H$_2$; 60 sccm/min N$_2$) at a temperature of about 225° C., pressure of 200 psig (about 1400 KPag), and GHSV=6570 hr$^{-1}$. SiO$_2$ stabilized with 5% CaSiO$_3$ in hydrogenation of acetic acid was studied in a run of 15 hours duration at 225° C. using a fixed bed continuous reactor system to produce mainly ethanol, acetaldehyde, and ethyl acetate through hydrogenation and esterification reactions in a typical range of operating conditions employing 2.5 ml solid catalyst (14/30 mesh, diluted 1:1 (v/v, with quartz chips, 14/30 mesh). FIG. 3A illustrates the selectivity, and FIG. 3B illustrates the productivity of the catalysts as a function of time on-stream during the initial portion of the catalysts life. From the results of this example as reported in FIG. 3A and FIG. 3B, it can be appreciated that it is possible to attain a selectivity of over 90% and productivity of over 500 g of ethanol per kilogram of catalyst per hour.

Example 16

Catalyst Stability (Over 100 Hours)

Figures 4A, 4B:
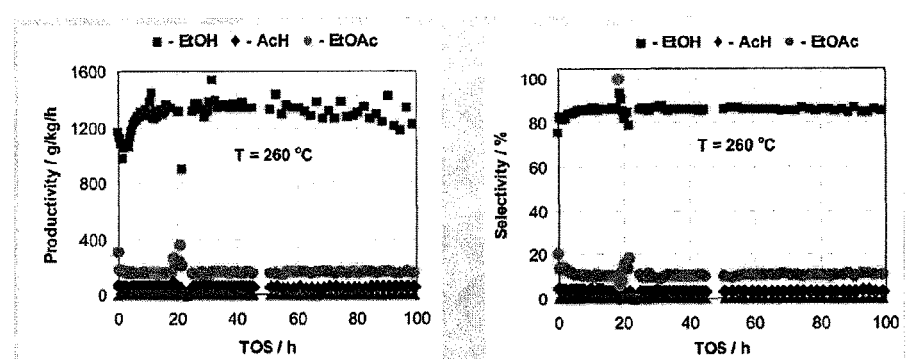
FIG. 4A is a graph of the productivity of a catalyst to ethanol over 100 hours of testing according to another embodiment of the invention.
FIG. 4B is a graph of the selectivity of the catalyst of FIG. 4A to ethanol.

Catalyst Stability: SiO$_2$—CaSiO$_3$(5)-Pt(3)-Sn(1.8). The catalytic performance and initial stability of SiO$_2$—CaSiO$_3$(5)-Pt(3)-Sn(1.8) was evaluated at constant temperature (260° C. over 100 hrs of reaction time. Only small changes in catalyst performance and selectivity were observed over the 100 hrs of total reaction time. Acetaldehyde appeared to be the only side product, and its concentration (~3 wt. %) remained largely unchanged over the course of the experiment. A summary of catalyst productivity and selectivity is provided in FIGS. 4A and 4B.

TABLE 4

| | | Reaction Conditions | | | | | Selectivity (%) | |
|---|---|---|---|---|---|---|---|---|
| Cat. Ex. | Cat. | Ratio of H$_2$:AcOH | Press. (KPa) | Temp. (° C.) | GHSV (hr$^{-1}$) | Conv. of AcOH (%) | EtOAc | EtOH |
| Inventive | | | | | | | | |
| 1 | SiO$_2$—CaSiO$_3$(5)-Pt(3)-Sn(1.8) | 5:1 | 2200 | 250 | 2500 | 24 | 6 | 92 |
| 2 | KA160-CaSiO$_3$(8)-Pt(3)-Sn(1.8) | 5:1 | 2200 | 250 | 2500 | 43 | 13 | 84 |
| 3 | SiO$_2$—CaSiO$_3$(2.5)-Pt(1.5)-Sn(0.9) | 10:1 | 1400 | 250 | 2500 | 26 | 8 | 86 |
| 4 | SiO$_2$ + MgSiO$_3$—Pt(1.0)-Sn(1.0) | 4:1 | 1400 | 250 | 6570 | 22 | 10 | 88 |
| 5 | SiO$_2$—CaSiO$_3$(5)-Re(4.5)-Pd(1) | 5:1 | 1400 | 250 | 6570 | 8 | 17 | 83 |
| 6 | SiO$_2$—ZnO(5)-Pt(1)-Sn(1) | 4:1 | 1400 | 275 | 6570 | 22 | 21 | 76 |
| Comparative | | | | | | | | |
| 7 | TiO$_2$—CaSiO$_3$(5)-Pt(3)-Sn(1.8) | 5:1 | 1400 | 250 | 6570 | 38 | 78 | 22 |
| 8 | Sn(0.5) on SiO$_2$ | 9:1~8:1 | 2200 | 250 | 2500 | 10 | | 1 |
| 9 | Pt(2)-Sn(2) on SiO$_2$ | 5:1 | 1400 | 296 | 6570 | 34 | 64 | 33 |
| 9 | Pt(2)-Sn(2) on SiO$_2$ | 5:1 | 1400 | 280 | 6570 | 37 | 62 | 36 |
| 9 | Pt(2)-Sn(2) on SiO$_2$ | 5:1 | 1400 | 250 | 6570 | 26 | 63 | 36 |
| 9 | Pt(2)-Sn(2) on SiO$_2$ | 5:1 | 1400 | 225 | 6570 | 11 | 57 | 42 |
| 10 | KA160-Pt(3)-Sn(1.8) | 5:1 | 2200 | 250 | 2500 | 61 | 50 | 47 |
| 11 | SiO$_2$—SnO$_2$(5)-Pt(1)-Zn(1) | 4:1 | 1400 | 275 | 6570 | 13 | 44 | 48 |
| 12 | SiO$_2$—TiO$_2$(10)-Pt(3)-Sn(1.8) | 5:1 | 1400 | 250 | 6570 | 73 | 53 | 47 |
| 13 | SiO$_2$—WO$_3$(10)-Pt(3)-Sn(1.8) | 5:1 | 1400 | 250 | 6570 | 17 | 23 | 77 |

Example 17

Catalyst Stability

Figures 5A, 5B:
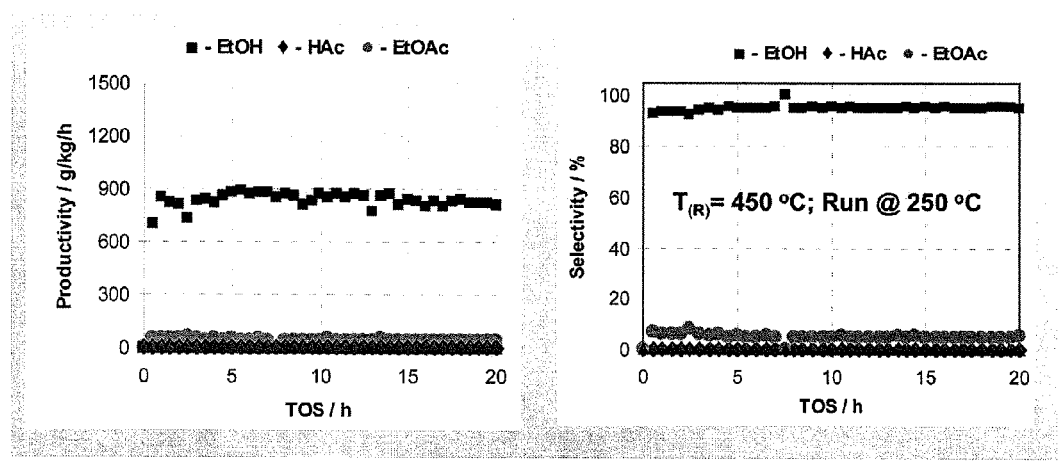
FIG. 5A is a graph of productivity of a catalyst to ethanol over 20 hours of testing according to another embodiment of the invention.
FIG. 5B is a graph of the selectivity of the catalyst of FIG. 5A to ethanol.

The procedure of Example 16 was repeated at a temperature of about 250° C. FIGS. 5A and 5B illustrate the productivity and selectivity of the catalysts as a function of time on-stream during the initial portion of the catalysts life. From the results of this example, as reported in FIGS. 5A and 5B, it can be appreciated, that it is still possible to attain a selectivity activity of over 90% but with productivity of over 800 g of ethanol per kilogram of catalyst per hour at this temperature.

Example 18

The catalyst of Example 3 was prepared with different loadings of support modifier, $CaSiO_3$, and produced the following catalysts: (i) $SiO_2$—Pt(1.5)-Sn(0.9); (ii) $SiO_2$—CaSiO$_3$(2.5)-Pt(1.5)-Sn(0.9); (iii) $SiO_2$—CaSiO$_3$(5.0)-Pt(1.5)-Sn(0.9); (iv) $SiO_2$—CaSiO$_3$(7.5)-Pt(1.5)-Sn(0.9); and (v) $SiO_2$—CaSiO$_3$(10)-Pt(1.5)-Sn(0.9). Each catalyst was used in hydrogenating acetic acid at 250° C. and 275° C. under similar conditions, i.e., 1400 bar (200 psig), GHSV of 2500 hr$^{-1}$ and a 10:1 hydrogen to acetic acid molar feed ratio, (683 sccm/min of $H_2$ to 0.183 g/min AcOH). The conversion is shown in FIG. 6A, productivity in FIG. 6B, selectivity at 250° C. in FIG. 6C and selectivity at 275° C. in FIG. 6D.

As shown in FIG. 6A, the conversion of acetic acid at 250° C. and 275° C. surprisingly increased at $CaSiO_3$ loadings greater than 2.5 wt. %. The initial drop in conversion exhibited from 0 to 2.5 wt. % $CaSiO_3$ would suggest that conversion would be expected to decrease as more $CaSiO_3$ is added. This trend, however, surprisingly reserves as more support modifier is added. Increasing conversion also results in increased productivity, as shown in FIG. 6B. The selectivities in FIGS. 6C and 6C show a slight increase as the amount of support modifier increases.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:
1. A process for producing ethanol, comprising:
hydrogenating acetic acid in the presence of a catalyst comprising:

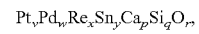

wherein:
(i) the ratio of v:y is between 3:2 and 2:3, and/or (ii) the ratio of w:x is between 1:3 and 1:5; and
p and q are selected such that p:q is from 1:20 to 1:200 with r being selected to satisfy valence requirements and v and w being selected such that:

$$0.005 \leq \frac{(3.25v + 1.75w)}{q} \leq 0.05.$$

2. The process of claim 1, wherein the ratio of v:y is between 3:2 and 2:3.
3. The process of claim 1, wherein the ratio of w:x is between 1:3 and 1:5.
4. A process for producing ethanol, comprising:
hydrogenating acetic acid in the presence of a catalyst comprising:

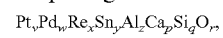

wherein:
(i) v and y are between 3:2 and 2:3, and/or (ii) w and x are between 1:3 and 1:5; and
p and z and the relative locations of aluminum and calcium atoms present are controlled such that Brønsted acid sites present upon the surface thereof are balanced by a support modifier; and
p and q are selected such that p:q is from 1:20 to 1:200 with r being selected to satisfy valence requirements, and
v and w are selected such that:

$$0.005 \leq \frac{(3.25v + 1.75w)}{q} \leq 0.05.$$

5. The process of claim 4, wherein the ratio of v:y is between 3:2 and 2:3.
6. The process of claim 4, wherein the ratio of w:x is between 1:3 and 1:5.
7. The process of claim 4, wherein the at least one support modifier is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

* * * * *